United States Patent
Atkins et al.

(10) Patent No.: US 12,201,767 B2
(45) Date of Patent: Jan. 21, 2025

(54) AEROSOL DEVICES HAVING COMPARTMENTALIZED MATERIALS

(71) Applicant: JUUL Labs, Inc., San Francisco, CA (US)

(72) Inventors: Ariel Atkins, San Francisco, CA (US); Adam Bowen, San Mateo, CA (US); Alexander Gould, San Francisco, CA (US); Chenyue Xing, San Francisco, CA (US)

(73) Assignee: JUUL Labs, Inc., Washington, DC (US)

(*) Notice: Subject to any disclaimer, the term of this patent is extended or adjusted under 35 U.S.C. 154(b) by 186 days.

(21) Appl. No.: 16/095,676

(22) PCT Filed: Apr. 21, 2017

(86) PCT No.: PCT/US2017/028977
§ 371 (c)(1),
(2) Date: Oct. 22, 2018

(87) PCT Pub. No.: WO2017/185051
PCT Pub. Date: Oct. 26, 2017

(65) Prior Publication Data
US 2019/0124982 A1    May 2, 2019

Related U.S. Application Data

(60) Provisional application No. 62/326,641, filed on Apr. 22, 2016.

(51) Int. Cl.
*A24F 40/30*    (2020.01)
*A24F 40/10*    (2020.01)
(Continued)

(52) U.S. Cl.
CPC ............ *A61M 15/06* (2013.01); *A24F 40/30* (2020.01); *A61M 11/042* (2014.02);
(Continued)

(58) Field of Classification Search
CPC ......... A24F 47/008; A24F 40/30; A24F 40/10
See application file for complete search history.

(56) References Cited

U.S. PATENT DOCUMENTS

720,007 A    2/1903   Dexter
1,165,000 A  12/1915  Dula
(Continued)

FOREIGN PATENT DOCUMENTS

CA    2641869 A1    5/2010
CA    2940842 A1    9/2015
(Continued)

OTHER PUBLICATIONS

U.S. Appl. No. 14/304,847, filed May 19, 2020, U.S. Pat. No. 10,653,180.
(Continued)

*Primary Examiner* — Christopher M Rodd
*Assistant Examiner* — Jennifer A Kessie
(74) *Attorney, Agent, or Firm* — Mintz Levin Cohn Ferris Glovsky and Popeo, P.C.

(57) ABSTRACT

A system for aerosolization of compartmentalized materials is provided. In some implementations, the system performs operations comprising vaporizing, by a heater, at least a portion of a first material to form a first vapor, wherein the first material is stored in a reservoir coupled to the heater. The operations can further comprise providing, through a draw channel comprising the heater, the first vapor to a second material within the draw channel, wherein the second material comprises one or more of nicotine and an acid, wherein the second material is positioned between the
(Continued)

resistive heater and an exit point of the draw channel. The operations can also include forming, based on the first vapor passing through and/or around the second material, an inhalable vapor. Related systems, methods, apparatuses, and articles of manufacture are also described.

19 Claims, 13 Drawing Sheets

(51) Int. Cl.
    *A24F 40/20*     (2020.01)
    *A24F 40/40*     (2020.01)
    *A61M 11/04*     (2006.01)
    *A61M 15/00*     (2006.01)
    *A61M 15/06*     (2006.01)
    *A61M 15/08*     (2006.01)

(52) U.S. Cl.
    CPC ......... *A61M 15/0003* (2014.02); *A24F 40/10* (2020.01); *A24F 40/20* (2020.01); *A24F 40/40* (2020.01); *A61M 15/08* (2013.01); *A61M 2205/3653* (2013.01); *A61M 2205/584* (2013.01); *A61M 2205/8206* (2013.01)

(56) References Cited

U.S. PATENT DOCUMENTS

| | | |
|---|---|---|
| 2,158,928 A | 5/1939 | Sol |
| 3,292,634 A | 12/1966 | Beucler |
| 4,303,083 A | 12/1981 | Burruss |
| 4,708,151 A | 11/1987 | Shelar |
| 4,771,796 A | 9/1988 | Myer |
| 5,101,838 A | 4/1992 | Burger |
| 5,144,962 A | 9/1992 | Counts et al. |
| 5,152,456 A | 10/1992 | Ross et al. |
| 5,159,942 A | 11/1992 | Brinkley et al. |
| 5,261,424 A | 11/1993 | Sprinkel, Jr. |
| 5,497,791 A | 3/1996 | Bowen et al. |
| 5,529,078 A | 6/1996 | Rehder et al. |
| 5,564,442 A | 10/1996 | Macdonald et al. |
| 5,708,258 A | 1/1998 | Counts et al. |
| 6,095,153 A | 8/2000 | Kessler et al. |
| 6,513,524 B1 | 2/2003 | Storz |
| 6,603,924 B2 | 5/2003 | Brown et al. |
| 6,772,756 B2 | 8/2004 | Shayan |
| 7,040,314 B2 | 5/2006 | Nguyen et al. |
| 7,434,584 B2 | 10/2008 | Steinberg |
| 7,832,410 B2 | 11/2010 | Hon |
| 8,371,310 B2 | 2/2013 | Brenneise |
| 8,714,150 B2 | 5/2014 | Alelov |
| 8,752,545 B2 | 6/2014 | Buchberger |
| 8,794,231 B2 | 8/2014 | Thorens et al. |
| 8,833,364 B2 | 9/2014 | Buchberger |
| 8,881,737 B2 | 11/2014 | Collett et al. |
| 8,910,639 B2 | 12/2014 | Chang et al. |
| 8,948,578 B2 | 2/2015 | Buchberger |
| 9,078,473 B2 | 7/2015 | Worm et al. |
| 9,282,772 B2 | 3/2016 | Tucker et al. |
| 9,301,547 B2 | 4/2016 | Liu |
| 9,364,800 B2 | 6/2016 | Dubief |
| 9,462,832 B2 | 10/2016 | Lord |
| 9,497,999 B2 | 11/2016 | Lord |
| 9,609,893 B2 | 4/2017 | Novak et al. |
| 9,675,109 B2 | 6/2017 | Monsees et al. |
| 9,717,276 B2 | 8/2017 | Brammer et al. |
| 9,839,238 B2 | 12/2017 | Worm et al. |
| 9,913,493 B2 | 3/2018 | Worm et al. |
| 9,943,108 B2 | 4/2018 | Lord |
| 9,974,335 B2 | 5/2018 | Lord |
| 10,111,466 B2 | 10/2018 | Lord |
| 10,194,689 B2 | 2/2019 | Schennum et al. |
| 10,206,429 B2 | 2/2019 | Davis et al. |
| 10,278,421 B2 | 5/2019 | Lord |
| 10,278,424 B2 | 5/2019 | Garthaffner et al. |
| 10,368,580 B2 | 8/2019 | Rostami et al. |
| 10,375,990 B2 | 8/2019 | Lord |
| 10,609,958 B2 | 4/2020 | Robinson et al. |
| 10,653,180 B2 | 5/2020 | Monsees et al. |
| 11,589,617 B2 | 2/2023 | Yilmaz |
| 2002/0146242 A1 | 10/2002 | Vieira |
| 2005/0016550 A1 | 1/2005 | Katase |
| 2005/0067503 A1 | 3/2005 | Katase |
| 2005/0150488 A1 | 7/2005 | Dave |
| 2007/0006889 A1 | 1/2007 | Kobal et al. |
| 2008/0023003 A1 | 1/2008 | Rosenthal |
| 2008/0092912 A1 | 4/2008 | Robinson et al. |
| 2008/0257367 A1 | 10/2008 | Paterno et al. |
| 2009/0095287 A1 | 4/2009 | Emarlou |
| 2009/0133691 A1 | 5/2009 | Yamada et al. |
| 2009/0151717 A1 | 6/2009 | Bowen et al. |
| 2009/0230117 A1 | 9/2009 | Fernando et al. |
| 2009/0255534 A1 | 10/2009 | Paterno |
| 2009/0283103 A1 | 11/2009 | Nielsen et al. |
| 2009/0293892 A1 | 12/2009 | Williams et al. |
| 2009/0302019 A1 | 12/2009 | Selenski et al. |
| 2009/0314299 A1 | 12/2009 | Kilpatrick |
| 2010/0006092 A1 | 1/2010 | Hale et al. |
| 2010/0200006 A1 | 8/2010 | Robinson et al. |
| 2010/0313901 A1 | 12/2010 | Fernando et al. |
| 2011/0030706 A1 | 2/2011 | Gibson et al. |
| 2011/0036346 A1 | 2/2011 | Cohen et al. |
| 2011/0126831 A1 | 6/2011 | Fernandez |
| 2011/0209717 A1 | 9/2011 | Han |
| 2011/0265806 A1 | 11/2011 | Alarcon et al. |
| 2012/0006343 A1 | 1/2012 | Renaud et al. |
| 2012/0048266 A1 | 3/2012 | Alelov |
| 2012/0199146 A1 | 8/2012 | Marangos |
| 2012/0199572 A1 | 8/2012 | Shen et al. |
| 2012/0255546 A1 | 10/2012 | Goetz et al. |
| 2012/0260927 A1 | 10/2012 | Liu |
| 2012/0325227 A1 | 12/2012 | Robinson et al. |
| 2013/0014772 A1 | 1/2013 | Liu |
| 2013/0160780 A1 | 6/2013 | Matsumoto et al. |
| 2013/0220315 A1 | 8/2013 | Conley et al. |
| 2013/0255702 A1 | 10/2013 | Griffith et al. |
| 2013/0298905 A1 | 11/2013 | Levin et al. |
| 2014/0000638 A1* | 1/2014 | Sebastian ............... A24F 47/008 131/328 |
| 2014/0096782 A1 | 4/2014 | Ampolini et al. |
| 2014/0123989 A1 | 5/2014 | LaMothe |
| 2014/0190503 A1 | 7/2014 | Li et al. |
| 2014/0209105 A1 | 7/2014 | Sears et al. |
| 2014/0238424 A1* | 8/2014 | Macko .................... A24F 40/46 131/328 |
| 2014/0261486 A1 | 9/2014 | Potter et al. |
| 2014/0261487 A1 | 9/2014 | Chapman et al. |
| 2014/0261491 A1 | 9/2014 | Hawes |
| 2014/0345631 A1 | 11/2014 | Bowen et al. |
| 2014/0345635 A1 | 11/2014 | Rabinowitz et al. |
| 2014/0366898 A1* | 12/2014 | Monsees ............... A24F 47/008 131/329 |
| 2014/0366902 A1 | 12/2014 | Chiolini et al. |
| 2015/0047662 A1 | 2/2015 | Hopps |
| 2015/0101606 A1 | 4/2015 | White |
| 2015/0128966 A1 | 5/2015 | Lord |
| 2015/0136153 A1 | 5/2015 | Lord |
| 2015/0157055 A1 | 6/2015 | Lord |
| 2015/0196059 A1 | 7/2015 | Liu |
| 2015/0216236 A1 | 8/2015 | Bless et al. |
| 2015/0237917 A1 | 8/2015 | Lord |
| 2015/0245659 A1 | 9/2015 | Depiano et al. |
| 2015/0245669 A1 | 9/2015 | Cadieux et al. |
| 2015/0258289 A1 | 9/2015 | Henry et al. |
| 2015/0305409 A1 | 10/2015 | Verleur et al. |
| 2015/0313284 A1 | 11/2015 | Liu |
| 2015/0335070 A1 | 11/2015 | Sears et al. |
| 2015/0374035 A1 | 12/2015 | Sanchez et al. |
| 2016/0007653 A1 | 1/2016 | Tu |
| 2016/0007654 A1 | 1/2016 | Zhu |
| 2016/0021934 A1 | 1/2016 | Cadieux et al. |
| 2016/0044967 A1 | 2/2016 | Bowen et al. |
| 2016/0073693 A1 | 3/2016 | Reevell |

(56) References Cited

U.S. PATENT DOCUMENTS

| | | |
|---|---|---|
| 2016/0081395 A1 | 3/2016 | Thorens et al. |
| 2016/0106155 A1 | 4/2016 | Reevell |
| 2016/0120218 A1 | 5/2016 | Schennum et al. |
| 2016/0206000 A1 | 7/2016 | Lord et al. |
| 2016/0219934 A1 | 8/2016 | Li et al. |
| 2016/0242466 A1 | 8/2016 | Lord et al. |
| 2016/0249682 A1 | 9/2016 | Leadley et al. |
| 2016/0262453 A1 | 9/2016 | Ampolini et al. |
| 2016/0262454 A1 | 9/2016 | Sears et al. |
| 2016/0262459 A1 | 9/2016 | Monsees et al. |
| 2016/0309786 A1 | 10/2016 | Holtz et al. |
| 2016/0331026 A1 | 11/2016 | Cameron |
| 2016/0331030 A1 | 11/2016 | Ampolini et al. |
| 2016/0331034 A1 | 11/2016 | Cameron |
| 2017/0027226 A1 | 2/2017 | Mironov et al. |
| 2017/0035113 A1 | 2/2017 | Thorens |
| 2017/0127722 A1 | 5/2017 | Davis et al. |
| 2017/0127725 A1 | 5/2017 | Buchberger et al. |
| 2017/0135399 A1 | 5/2017 | Gavrielov et al. |
| 2017/0135401 A1 | 5/2017 | Dickens |
| 2017/0143038 A1 | 5/2017 | Dickens |
| 2017/0143041 A1 | 5/2017 | Batista et al. |
| 2017/0156403 A1 | 6/2017 | Gill et al. |
| 2017/0164657 A1 | 6/2017 | Batista |
| 2017/0181471 A1 | 6/2017 | Phillips et al. |
| 2017/0188626 A1 | 7/2017 | Davis et al. |
| 2017/0188629 A1 | 7/2017 | Dickens et al. |
| 2017/0196268 A1 | 7/2017 | Reevell |
| 2017/0208857 A1 | 7/2017 | Branton et al. |
| 2017/0224014 A1 | 8/2017 | Fraser |
| 2017/0231284 A1 | 8/2017 | Newns |
| 2017/0245543 A1 | 8/2017 | Karles et al. |
| 2017/0251721 A1 | 9/2017 | Rostami et al. |
| 2017/0258134 A1 | 9/2017 | Kane |
| 2017/0258137 A1 | 9/2017 | Smith et al. |
| 2017/0258138 A1 | 9/2017 | Rostami et al. |
| 2017/0265524 A1 | 9/2017 | Cadieux et al. |
| 2017/0280767 A1 | 10/2017 | Li et al. |
| 2017/0280768 A1 | 10/2017 | Lipowicz |
| 2017/0283154 A1 | 10/2017 | Karles et al. |
| 2017/0290370 A1 | 10/2017 | Garthaffner et al. |
| 2017/0303586 A1 | 10/2017 | Sur |
| 2017/0325502 A1 | 11/2017 | Nelson et al. |
| 2017/0325506 A1 | 11/2017 | Batista |
| 2017/0333650 A1 | 11/2017 | Buchberger et al. |
| 2017/0347706 A1 | 12/2017 | Aoun et al. |
| 2018/0000158 A1 | 1/2018 | Ewing et al. |
| 2018/0016040 A1 | 1/2018 | Ewing et al. |
| 2018/0027875 A1 | 2/2018 | Rostami et al. |
| 2018/0027879 A1 | 2/2018 | Gavrielov et al. |
| 2018/0035717 A1 | 2/2018 | Batista |
| 2018/0070633 A1 | 3/2018 | Phillips et al. |
| 2018/0070641 A1 | 3/2018 | Batista et al. |
| 2018/0085539 A1 | 3/2018 | Trzecieski |
| 2018/0132525 A1 | 5/2018 | Patil et al. |
| 2018/0160733 A1 | 6/2018 | Leadley et al. |
| 2018/0168227 A1 | 6/2018 | Fraser et al. |
| 2018/0169357 A1 | 6/2018 | Reevell |
| 2018/0184712 A1 | 7/2018 | Fraser et al. |
| 2018/0192700 A1 | 7/2018 | Fraser et al. |
| 2018/0271151 A1 | 9/2018 | Litten |
| 2018/0271154 A1 | 9/2018 | Leadley et al. |
| 2018/0271155 A1 | 9/2018 | Baker et al. |
| 2018/0279679 A1 | 10/2018 | Mcadam et al. |
| 2018/0343920 A1 | 12/2018 | Sutton et al. |
| 2018/0360123 A1 | 12/2018 | Silvestrini |
| 2018/0368472 A1 | 12/2018 | Mishra et al. |
| 2019/0014825 A1 | 1/2019 | Saygili |
| 2019/0021399 A1 | 1/2019 | Silvestrini |
| 2019/0029320 A1 | 1/2019 | Saygili |
| 2019/0045837 A1 | 2/2019 | Spencer |
| 2019/0046745 A1 | 2/2019 | Nettenstrom et al. |
| 2019/0083720 A1 | 3/2019 | Leadley et al. |
| 2019/0098930 A1 | 4/2019 | Fallon et al. |
| 2019/0098931 A1 | 4/2019 | Leadley et al. |
| 2019/0099561 A1 | 4/2019 | Nettenstrom |
| 2019/0099562 A1 | 4/2019 | Nettenstrom et al. |
| 2019/0099567 A1 | 4/2019 | Nettenstrom et al. |
| 2019/0150520 A1 | 5/2019 | Fraser et al. |
| 2019/0208821 A1* | 7/2019 | Fraser .............. H05B 1/0297 |
| 2019/0208822 A1 | 7/2019 | Mullin |
| 2019/0208824 A1 | 7/2019 | Wright |
| 2019/0223508 A1 | 7/2019 | Otiaba et al. |
| 2019/0246693 A1 | 8/2019 | Nettenstrom et al. |
| 2019/0320718 A1 | 10/2019 | Yilmaz |
| 2020/0000151 A1 | 1/2020 | Fraser et al. |
| 2020/0029618 A1 | 1/2020 | Fraser et al. |
| 2020/0037669 A1 | 2/2020 | Bowen et al. |
| 2020/0038601 A1 | 2/2020 | Hepworth et al. |
| 2020/0046025 A1 | 2/2020 | Otiaba et al. |
| 2020/0107572 A1 | 4/2020 | Marques Borges et al. |
| 2020/0113234 A1 | 4/2020 | Patoret |
| 2020/0146352 A1 | 5/2020 | Alston et al. |
| 2020/0154771 A1 | 5/2020 | Otiaba et al. |
| 2020/0163376 A1 | 5/2020 | Saygili et al. |
| 2020/0221777 A1 | 7/2020 | Saygili et al. |
| 2020/0260783 A1 | 8/2020 | Waller et al. |
| 2020/0275696 A1 | 9/2020 | Atkins et al. |
| 2021/0084986 A1 | 3/2021 | Hepworth et al. |
| 2021/0145051 A1 | 5/2021 | Florack et al. |
| 2021/0145072 A1 | 5/2021 | Mullin et al. |

FOREIGN PATENT DOCUMENTS

| | | |
|---|---|---|
| CN | 1541577 A | 11/2004 |
| CN | 201630238 U | 11/2010 |
| CN | 102612361 A | 7/2012 |
| CN | 202738816 U | 2/2013 |
| CN | 202873796 U | 4/2013 |
| CN | 103156273 A | 6/2013 |
| CN | 103929985 A | 7/2014 |
| CN | 203748667 U | 8/2014 |
| CN | 104544567 A | 4/2015 |
| CN | 104684422 A | 6/2015 |
| CN | 204409589 U | 6/2015 |
| CN | 104770878 A | 7/2015 |
| CN | 102762118 B | 8/2015 |
| CN | 104968225 A | 10/2015 |
| CN | 204837995 U | 12/2015 |
| CN | 105473012 B | 6/2020 |
| EP | 3085257 A1 | 10/2016 |
| EP | 2753200 B1 | 12/2017 |
| EP | 2961288 B1 | 10/2018 |
| EP | 2961285 B1 | 1/2019 |
| EP | 3344080 B1 | 6/2020 |
| EP | 3285843 B1 | 9/2020 |
| EP | 3481473 B1 | 9/2020 |
| EP | 3484315 B1 | 12/2020 |
| EP | 3525608 B1 | 12/2020 |
| EP | 3562337 B1 | 2/2021 |
| EP | 3522740 B1 | 3/2021 |
| EP | 3232838 B1 | 4/2021 |
| EP | 3562535 B1 | 4/2021 |
| EP | 3534733 B1 | 6/2021 |
| EP | 3554295 B1 | 7/2021 |
| EP | 3104723 B1 | 8/2021 |
| EP | 3573486 B1 | 9/2021 |
| EP | 3644770 B1 | 9/2021 |
| GB | 1025630 A | 4/1966 |
| GB | 1213318 A | 11/1970 |
| GB | 2524779 A | 10/2015 |
| JP | 2005058421 A | 3/2005 |
| KR | 20130052119 A | 5/2013 |
| KR | 10-2016-0112770 A | 9/2016 |
| KR | 101691984 B1 | 1/2017 |
| WO | WO-03082031 A1 | 10/2003 |
| WO | WO-2004064548 A1 | 8/2004 |
| WO | WO-2004089126 A1 | 10/2004 |
| WO | WO-2010140841 A2 | 12/2010 |
| WO | WO-2012/065310 A1 | 5/2012 |
| WO | WO-2015150699 A1 | 10/2015 |
| WO | WO-2016/062777 A1 | 4/2016 |
| WO | WO-2016/079589 A1 | 5/2016 |
| WO | WO-2016/135342 A2 | 9/2016 |

(56) References Cited

FOREIGN PATENT DOCUMENTS

| WO | WO-2016/179376 A1 | 11/2016 |
| WO | WO-2017042081 A1 | 3/2017 |
| WO | WO-2017153591 A1 | 9/2017 |
| WO | WO-2017185051 A1 | 10/2017 |
| WO | WO-2017/207443 A1 | 12/2017 |
| WO | WO-2018/029186 A1 | 2/2018 |
| WO | WO-2019122880 A1 | 6/2019 |
| WO | WO-2020081849 A2 | 4/2020 |
| WO | WO-2020201026 A1 | 8/2020 |

OTHER PUBLICATIONS

U.S. Appl. No. 16/877,043, filed May 18, 2020, US 2020-0275693.
Becker, et al. (Jul. 1, 1985) "PTC Heating Elements-Background Analysis and Design Attributes", 8095 IEEE Transactions on Industry Applications, IA-21(4):896-898.

* cited by examiner

FIG. 10

Check valve A 1115

Fluid Reservoir

Check valve B 1117

Side A 1118

Side B 1119

Valve A 1111

Valve B 1113

Air

Aerosol 1125 heater

Control system 1122

Battery 1124

FIG. 11

AEROSOL DEVICES HAVING COMPARTMENTALIZED MATERIALS

CROSS REFERENCE TO RELATED APPLICATIONS

This application is a U.S. national stage application of PCT/US2017/028977, filed on Apr. 21, 2017 and entitled "AEROSOL DEVICES HAVING COMPARTMENTALIZED MATERIALS", which claims priority to U.S. Provisional Patent Application No. 62/326,641, filed on Apr. 22, 2016 and entitled "VAPORIZERS HAVING COMPARTMENTALIZED VAPORIZABLE MATERIALS," the disclosure of which is incorporated herein by reference in its entirety.

FIELD

The subject matter described herein relates to systems and methods for providing inhalable aerosols, and more particularly, aerosol devices, cartridges for aerosol devices, aerosol systems, and methods for making, using, and/or delivering aerosol to a user.

BACKGROUND

Electronic inhalable aerosol devices (e.g., alternatively referred to as vaporizer devices, vaporization devices, electronic vaping devices, etc.) and particularly electronic aerosol devices, typically utilize a material that is "vaporized" to create an aerosol "vapor" (which may contain particles in a gas, liquid, and/or solid form) capable of delivering an active ingredient to a user. Such materials are typically compounded (e.g., combined) prior to adding to the vaporizer device.

Electronic vaporization devices, for example, nicotine vaporization devices, may include vaporizable compositions that, when compounded in advance or otherwise preformed, may have a limited shelf life ("freshness") and may be caustic or otherwise damaging to the vaporization devices (including cartridges holding the vaporizable material). Accordingly, it can be desirable to provide systems, methods, and/or apparatuses for separating one or more components of vaporizable materials.

SUMMARY

Described herein are vaporization apparatuses (e.g., devices, systems and compositions) and methods for using them to deliver an aerosol (e.g., vapor) in which separate reservoirs for component portions of the final vapor may be used and the final composition of the vapor may be formed by combining separately held components.

Nicotine is an alkaloid molecule that comprises two basic nitrogen atoms. It may occur in different states of protonation. For example, if no protonation exists, nicotine is referred to as the "free base." If one nitrogen (atom) is protonated, then the nicotine would be "mono-protonated." In some aspects, nicotine salt formulations may be formed by adding a suitable acid to nicotine, stirring the neat mixture at ambient temperature or at elevated temperature, and then diluting the neat mixture with a carrier mixture, such as a mixture of propylene glycol and glycerin.

Different nicotine salt formulations produce varying degrees of satisfaction in an individual. For example, the extent of protonation of the nicotine salt affects satisfaction, such that more protonation is more satisfying as compared to less protonation. Accordingly, the nicotine salt formed may be monoprotonated, di-protonated, or may exist in more than one protonation state, e.g., an equilibrium of deprotonated, mono-protonated and di-protonated nicotine salts.

In accordance with the teachings of the present disclosure, described herein are vaporization methods, and devices for forming and/or delivering nicotine salt formulations including vapor aerosol compositions comprising protonated nicotine in which the final vapor composition can include protonated nicotine (e.g., between 0.1% and 20%, between 0.5% and 15%, between 1% and 10%, etc.), an acid (e.g., an organic acid from among a specific subset of acids forming nicotine salts (e.g., having a high $T_{max}$ as described herein) and/or a biologically acceptable liquid carrier (e.g., a vegetable glycerol, a glycol, and/or the like).

Although the vaporizer methods and apparatuses (devices and systems) described herein are described in the context of nicotine vaporizers, the principles described herein may be applied to different vaporizable materials as well, including one or more active ingredients of plant material, a botanical, other herbs, and/or some combination thereof.

For example, described herein are methods of generating an aerosol using a vaporization device (e.g., methods of delivering a vapor of nicotine) in which one or more components of a nicotine formulation to be vaporized are separately stored and/or separately vaporized by the vaporization device. In some aspects, methods described herein can include generating an aerosol (also referred to herein as "vapor") and/or protonated nicotine. Devices for generating an aerosol of protonated nicotine can include one or more of nicotine, acid, and/or a biologically acceptable liquid carrier stored separately from the other components, and/or combined in the aerosol delivered to the user.

Also described herein are methods and apparatuses in which the material to be delivered is stored in a precursor form (e.g., an acid precursor) that is activated or modified by the vaporization of the material so that the final vapor delivered by the apparatus includes a protonated nicotine (e.g., nicotine, acid and biologically acceptable liquid carrier). Any of the methods and apparatuses described herein may incorporate a precursor material, such as an acid precursor that forms an acid for protonating nicotine during vaporization.

Also described herein are methods and apparatuses for delivering a vapor of protonated nicotine in which one or more components (e.g., nicotine, acid, etc.) are added either simultaneously (e.g., close in time and/or including separate time periods which at least partially overlap) or sequentially in any order following the formation of a vapor, by eluting the one or more components from a liquid into the vapor. For example, a vapor (e.g., a vapor of a biologically acceptable carrier such a glycol and/or glycerol) can be passed around, along or through a sponge or other porous substrate holding a liquid solution of any nicotine, protonated nicotine, acid, flavorant, other component, and/or some combination thereof. Any of the methods or apparatuses described herein may include or be configured to include passing a vapor of a carrier (which may include nicotine and/or an acid) through one or more liquid solutions including a nicotine, protonated nicotine, acid, or any other material to be present in the final vapor composition to be delivered.

Also described herein are methods and apparatuses that may produce a vapor of protonated nicotine (e.g., including nicotine, an acid, and/or a biologically acceptable carrier) and also include a tobacco material (e.g., dried tobacco, oils of tobacco, etc.). The vapor may be passed through and/or around the tobacco material. The tobacco material may be warmed or heated, for example, to a temperature that is below the threshold for vaporization (e.g., below 150° C., 125° C., etc.). In some variations the temperature may be above vaporization but below combustion (e.g., less than 500° C., less than 400° C., less than 300° C., less than 200° C., less than 150° C., etc.). Any of these tobacco material warming temperatures may be above ambient temp (e.g., above 20° C., above 25° C., above 30° C., above 40° C., above 50° C., etc.) and/or below the maximum temperature (e.g., below 500° C., 400° C., 300° C., 200° CX, 150° C., 100° C., etc., including any combination of the minimum and maximum temperatures described herein such as between 50° C. and 500° C., between 100° C. and 200° C., between 100° C. and 150° C., between 100° C. and 125° C., etc.). Any of the methods and apparatuses described herein may include or be configured to include the use of a tobacco material.

Although the disclosure, including the figures, described herein may describe and/or exemplify different variations separately, it should be understood that all or some (e.g., including various components) may be combined. For example, any of the apparatuses and methods of forming a protonated nicotine in which nicotine and/or acid components of the vaporizable material are stored and/or vaporized separately, and combined into vapor particles, including protonated nicotine, acid, and/or a carrier, may also be used with elution of one or more materials (e.g., acid, flavorant, nicotine, etc.) by elution (e.g., through a sponge) and/or with passing the vapor through and/or around a tobacco material. Additionally or alternatively, any of these methods and apparatuses may include the use of an acid precursor that forms (following heating or other processing) the acid included in the emitted vapor with the protonated nicotine.

For example, described herein are vaporizers similar to those described in U.S. Patent Publication No. 2014/0366898, incorporated herein by reference, in which the acid or acid-forming component of the vapor is stored separately from the nicotine to be protonated in the vapor delivered to the user.

Thus, a method of generating an aerosol using a vaporizer device having two or more separate reservoirs may include vaporizing a first material contained in a first reservoir of the vaporizer device and a second material contained in a second reservoir of the vaporizer device (e.g., at/near the same time), where the first material comprises a carrier and nicotine, and where the second material comprises one or more of a flavorant, an acid, or an acid precursor that forms the acid upon heating.

A method of generating an aerosol using a vaporizer device having two or more separate reservoirs may include vaporizing a first material contained in a first reservoir of the vaporizer device and a second material contained in a second reservoir of the vaporizer device by heating one or more resistive heaters (e.g., at/near the same time), where the first material comprises a carrier and nicotine, and where the second material comprises a second carrier and one or more of a flavorant, an acid, or an acid precursor that forms the acid upon heating, to emit a vapor from the vaporizer device. The emitted vapor comprises between about 0.5% and 15% nicotine, acid, and the carrier, where the carrier comprises between about 10-90% vegetable glycerol, and where the rest (or at least a portion of the rest) comprises another glycol, such as propylene glycol.

For example, a method of generating an aerosol using a vaporizer device having two or more separate reservoirs comprises vaporizing a first material contained in a first reservoir of the vaporizer device with a first resistive heater and a second material contained in a second reservoir of the vaporizer device with a second resistive heater (e.g., at/near the same time), where the first material comprises a carrier and nicotine, and where the second material comprises an acid or an acid precursor that forms the acid upon heating, where vapor particles of the first material and vapor particles of the second material are combined into a vapor, and the vapor is emitted from the vaporizer device.

In general, the components of the vaporizable material (e.g., the nicotine solution, e.g., a solution of nicotine and a carrier material, the acid or acid precursor material, which may be in the same or a different carrier) may be stored separately in the device (including in devices configured, as any of the devices described herein may be, as cartridges) and the solutions may be "simultaneously" vaporized (e.g., mixing and vaporizing using a common atomizer/heater, or atomized separately and the resulting vapors combined and allowed to fuse or otherwise combine. For example, simultaneously vaporizing may comprise heating a single resistive heater to vaporize the first and second materials, and/or heating a first resistive heater to vaporize the first material and heating a second resistive heater to vaporize the second material at/near the same time. Where two or more heaters are used to vaporize the component materials forming the final vapor formulation, the heaters may be arranged in parallel in the vaporizer device or in series in the vaporization device. For example, simultaneously vaporizing may include heating a first resistive heater to vaporize the first material and heating a second resistive heater to vaporize the second material (e.g., at/near the same time), where the first and second resistive heaters are arranged in series in the vaporizer device. Simultaneously vaporizing may comprise heating a first (e.g., resistive) heater to vaporize the first material at a first temperature and heating the second (e.g., resistive) heater to vaporize the second material at a second temperature that is different from the first temperature (e.g., at/near the same time).

Any of the heaters described herein for vaporizing a material may additionally or alternatively be referred to as atomizers. In addition, any of these heaters may be resistive heaters, though other (non-resistive) types of heater may be used.

Heating of the vaporizable material (or material components) may be controlled by a controller (e.g., processor and/or memory configured to control heating and/or vaporizing) and may be controlled by controlling the power applied to the heater or heater circuitry. The heating may be done by holding at/near a single temperature or by adjusting a heating profile (e.g., controlling the heating temperature over time, or applying power to the heater over time). For example, simultaneously vaporizing may comprise heating a first resistive heater to vaporize the first material with a first temperature profile and heating the second resistive heater to vaporize the second material with a second temperature profile that is different from the first temperature profile (e.g., at/near the same time).

In some embodiments, the first material may comprise a carrier and nicotine or protonated nicotine, and the second material may comprise a second carrier and one or more of a flavorant and/or an organic acid.

Any of the methods described herein may include emitting vapor from the vaporizer device, where the emitted vapor comprises between about 0.5% and about 15% nicotine, an organic acid, and the carrier, and where the carrier comprises between about 90 and about 10% vegetable glycerol and a glycol. For example, emitting the vapor from the vaporizer device may comprise emitting vapor having between about 0.5% and about 15% nicotine, the organic acid, and the carrier, where the carrier comprises between about 90% and about 10% vegetable glycerol and a glycol.

Any of the methods described herein may include allowing a user to adjust the temperature applied to vaporize either the first and/or second material. Thus, in any of these variations, the user may adjust the heating and therefore vapor-forming of one or more of the component parts. For example, a method or an apparatus capable of performing the method may include allowing a user to adjust the temperature applied to vaporize one of the first material or the second material.

Any of the methods described herein may include combining vapor particles of the first material and vapor particles of the second material into a vapor. In any of the methods described herein, the first carrier and the second carrier may be the same or different.

Also described herein are vaporizer devices (e.g., cartridges, electronic cigarettes, etc.) that include two or more separate reservoirs for generating the inhalable aerosol (vapor) as described herein. For example, a vaporizer device having two or more separate reservoirs for generating an inhalable aerosol may include a first reservoir containing a first material, where the first material comprises a carrier and nicotine or protonated nicotine, a second reservoir containing a second material that is different from the first material, where the second material comprises an acid or an acid precursor that forms the acid upon heating, one or more atomizers in communication with the first reservoir and the second reservoir, and a controller configured to apply energy to the one or more atomizers to vaporize the first material and the second material to form vapor particles comprising the carrier, nicotine and the acid.

A vaporizer device having two or more separate reservoirs for generating an inhalable aerosol may include a first reservoir containing a first material, where the first material comprises a carrier and nicotine or protonated nicotine, a second reservoir containing a second material that is different from the first material, where the second material comprises an acid or an acid precursor that forms the acid upon heating, a first resistive heater in communication with the first reservoir, a second resistive heater in communication with the second reservoir, a controller configured to apply energy to the first resistive heater and the second resistive heater to separately heat the first material and the second material, and a chamber where vapor particles of the first material combine with vapor particles of the second material to form vapor particles comprising the carrier, nicotine or protonated nicotine and the acid.

As used herein, the term "in communication with" (and any variants thereof) can include various forms of interaction between two or more components, such as one or more of a physical contact/coupling of two or more components, an electrical contact/coupling of two or more components (whether wired or wireless, such as through the use of radio waves), in insertion of at least a portion of one component into at least a portion of another component, a heating of at least a portion of one component by at least a portion of another component (e.g., through conductive, convective, and/or radiative heat transfer), and/or the like.

In any of these methods and apparatuses, the atomizers (e.g., heaters) may include a first resistive heater in communication with the first reservoir and a second resistive heater in communication with the second reservoir. The one or more atomizers (e.g., heaters) may include a first resistive heater in communication with the first reservoir and a second resistive heater in communication with the second reservoir, and where the first and second resistive heaters are in parallel or in series.

Furthermore, any of the apparatuses described herein may include a chamber (e.g., channel, portion of a channel such as a draw channel, etc.) where vapor particles of the first material combine with vapor particles of the second material to form vapor particles comprising the carrier, nicotine, and the acid. The chamber may comprise a region of an airflow path through the device.

The separately contained components forming the final vapor (e.g., the first material, second material, third material, etc.) can include a liquid carrier and one or more of: nicotine, acid or acid precursor, flavorants, etc.). The nicotine and acid or acid precursor may preferentially be stored separately, so that protonation of the nicotine occurs after forming the vapor. In general, the concentration of nicotine in the component and/or final (vapor) may be between about 0.1 (w/w) and about 20% (w/w) nicotine (e.g., between 0.1% and about 15%, between 0.1% and 10%, between 0.1% and 8%, between 0.5% and 20%, between 0.5% and 15%, between 0.5% and 10%, between 0.5% and 8%, etc.). The carrier that is vaporized to form the vapor is preferably a glycerol and a glycol, such as a vegetable glycerol and a glycol. The glycerol may be any appropriate glycerol, such as in particular vegetable glycerol. The percentage of vegetable glycerol is preferably between 10% and 90% of the vapor (e.g., between 10% and 95%, between 10% and 90%, between 20% and 90%, between 30% and 90%, between 20% and 85%, between 30% and 85%, between 35% and 90%, between 35% and 80%, etc.). The carrier may also include any appropriate glycol (including propylene glycol). The glycol may make up the balance of the carrier not made up of glycerol. For example, in general the carrier is a vapor-forming medium and may also be referred to as a humectant. The carrier may comprise a ratio of vegetable glycerol to glycol (e.g., propylene glycol or other natural or synthetic glycol). The ratio of the glycerol to glycol may be about 100:0 vegetable glycerol to propylene glycol. The ratio may be about 90:10 vegetable glycerol to propylene glycol. The ratio may be about 80:20 vegetable glycerol to propylene glycol. The ratio may be about 70:30 vegetable glycerol to propylene glycol. The ratio may be about 60:40 vegetable glycerol to propylene glycol. The ratio may be about 50:50 vegetable glycerol to propylene glycol, etc.

In any of the variations in which component parts (e.g., nicotine, acid or acid precursor) are stored and/or vaporized separately, the carrier in the component parts may be the same or it may be different. For example, where a second material (that is stored and/or vaporized separately from the first material) may comprise a second carrier that is different from the first carrier. For example, in some variations the first and second carrier may both comprise between about 10-90% vegetable glycerol, and where the rest (or at least a portion of the rest) comprises another glycol, such as propylene glycol. In some variations the first carrier comprises vegetable glycerol and glycol, while the second carrier comprises water.

As mentioned above, also described herein are variations in which the acid is formed from an acid precursor during or immediately after vaporization. For example, any of the acids that may form an effective nicotine salt formulation (e.g., a nicotine salt formulation that produces a blood $T_{max}$ and/or $C_{max}$ as described in U.S. Patent App. Pub. No. 2016/0044967, incorporated herein by reference in its entirety) may be formed from a precursor that, when heated, e.g., by the heat of vaporization of the solution into which it is held, degrades into the desired acid. For example, a nicotine salt formulation (e.g., a protonated nicotine and acid in aqueous solution) may be formed by combining protonated nicotine with an acid precursor of the desired acid that, when exposed to heat, forms the acid. Acid precursors may include inorganic salts of the acids (e.g., sodium salts of carboxylic acids), esters of the acids (e.g., ethyl benzoate), and dimers of the acids or their salts (e.g., pyruvic acid dimer). For example, benzoic acid is one of the thermal decomposition products of sodium benzoate. Pyruvic acid may be produced from sodium pyruvate. Benzoic acid may also be produced from ethyl benzoate by base hydrolysis. Pyruvic acid dimer (or pyruvate salt dimer) is more stable at low temperature and can product pyruvic acid and other acids at high temperatures. Thus, in general, any of the methods and apparatuses described herein may include an acid precursor that degrades in the heat used to vaporize the carrier solution in which the acid precursor is held, to form an acid that may then protonate nicotine (e.g., freebase nicotine) as part of the nicotine salt producing a blood nicotine profile having a peak ($T_{max}$) within the first 3 to 8 minutes (e.g., inhalation of the aerosol into a user's lungs over a period of about 5 minutes at a rate of about one inhalation per 30 seconds results in a nicotine plasma $T_{max}$ from about 3 minutes to about 8 min).

For example, a method of delivering nicotine to a user from a vaporizer comprising protonated nicotine in a biologically acceptable liquid carrier, and an acid precursor may include: vaporizing the biologically acceptable liquid carrier and heating (e.g., at/near the same time) the acid precursor to form an acid; emitting a vapor comprising from about 0.5% (w/w) to about 20% (w/w) protonated nicotine, the acid, and the biologically acceptable liquid carrier.

Vaporizing may comprise vaporizing the biologically acceptable liquid carrier containing nicotine and the acid precursor to form the acid within the vapor without forming the acid from the acid precursor in the vaporizer. For example, a small/negligible amount of acid may be present in the unheated solution contained in the vaporizer (e.g., less than 20%, less than 15%, less than 10%, less than 5%, less than 2%, less than 1%, less than 0.5%, less than 0.1%, etc.).

Vaporizing the biologically acceptable liquid carrier and heating the acid precursor (e.g., at/near the same time) may comprise separately vaporizing the biologically acceptable liquid carrier and the acid precursor and allowing vapor particles of the biologically acceptable liquid carrier to combine with vapor particles of the acid formed by the acid precursor.

In any of the methods and apparatuses described herein, the molar ratio of nicotine or deprotonated nicotine to acid in the vapor may be between about 0.5:1 and about 1:5 (e.g., between about 0.7:1 and about 1:3, between about 0.9:1 and about 1:4, between about 0.9 to about 1 and 1:3, between about 1:1 and about 1:5, between about 1:1 and about 1:3, etc.).

In any of the methods and apparatuses described herein, the particle size of the emitted vapor may be from about 0.1 microns to about 5 microns.

As mentioned above, the acid precursor may be dissolved in the biologically acceptable liquid carrier (e.g., vegetable glycerol/propylene glycol, etc.).

In general, any of the methods described herein (and devices for performing the methods) may include vaporizing one or more of the vaporizable materials (or component materials) by heating the materials to about 100° C. and about 300° C.

In general, the acid precursor may be one or more of: an inorganic salt of the acid, an ester of the acid or a dimer of the acid. For example, the acid precursor may be one or more of: sodium benzoate, sodium pyruvate, ethyl benzoate, or pyruvic acid dimer. The acid precursor may be an acid precursor for benzoic acid.

For example, described herein is a method of delivering nicotine to a user from a vaporizer comprising nicotine in a biologically acceptable liquid carrier, and an acid precursor, the method comprising; vaporizing the biologically acceptable liquid carrier to form vapor, where the nicotine and the acid precursor are both in the biologically acceptable liquid carrier prior to vaporization, and where at least some of the acid precursor is formed into an acid by the vaporization; and emitting a vapor comprising from about 0.5% (w/w) to about 20% (w/w) nicotine or protonated nicotine, the acid, and the biologically acceptable liquid carrier.

A vaporizer device for delivering protonated nicotine to a user may include: a reservoir comprising from about 0.5% (w/w) and about 20% (w/w) nicotine and an acid precursor in a biologically acceptable liquid carrier; a resistive heater in communication with the reservoir; and a controller configured to apply energy to the resistive heater to vaporize the biologically acceptable liquid carrier into vapor particles comprising: an acid formed by the heat of vaporization from the acid precursor, from about 0.5% (w/w) and about 20% (w/w) nicotine or protonated nicotine, and the biologically acceptable liquid carrier.

In embodiments, a small amount of the acid may remain in the reservoir that holds the acid precursor as compared to the final amount in the vapor particles. For example, the reservoir(s) may comprise less than about 1% of the acid (w/w).

The biologically acceptable liquid carrier may comprise about 10-90% vegetable glycerol, and where the rest (or at least a portion of the rest) comprises another glycol, such as propylene glycol.

In any of the methods and apparatuses described herein, the reservoir may further comprise a flavorant.

The controller may be configured to emit vapor particles having a particle size from about 0.1 microns to about 5 microns.

Also described herein are vaporizer devices for delivering protonated nicotine to a user in which includes an acid precursor that forms the acid upon heating (vaporization). For example, a vaporizer devices for delivering protonated nicotine to a user may include a first reservoir comprising from 0.5% (w/w) and 20% (w/w) nicotine in a biologically acceptable liquid carrier; a second reservoir comprising an acid precursor; a first resistive heater in communication with both the first reservoir and the second reservoir; and a controller configured to apply energy to the first resistive heater to vaporize the biologically acceptable liquid carrier and the acid precursor into vapor, wherein the vapor comprises: an acid formed by the heat of vaporization from the acid precursor, from about 0.5% (w/w) and about 20% (w/w) protonated nicotine, and the biologically acceptable liquid carrier.

A vaporizer device for delivering protonated nicotine to a user may include: a first reservoir comprising from about 0.5% (w/w) and about 20% (w/w) nicotine in a biologically acceptable liquid carrier; a second reservoir comprising an acid precursor; a first resistive heater in communication with the first reservoir; a second resistive heater in communication with the second reservoir; and a controller configured to apply energy to the first resistive heater to vaporize the biologically acceptable liquid carrier and nicotine, and to apply energy to the second resistive heater to form vapor particles including an acid formed by the acid precursor; and a chamber or channel wherein the vapor of the biologically acceptable liquid carrier and nicotine combined with the vapor particles including the acid to form a vapor of protonated nicotine including from about 0.5% (w/w) and about 20% (w/w) protonated nicotine, the acid, and the biologically acceptable liquid carrier.

Any of the devices described herein may be configured as a cartridge that can be coupled (electrically and/or mechanically coupled) to a body that may include a power source (e.g., batter) and in some variations a controller (e.g., heater controller). For example, except as indicated otherwise, any of the devices described herein may be configured as cartridges (e.g., a cartridge device) for a vaporizer for delivering protonated nicotine to a user. For example, a cartridge device may include: a reservoir comprising from about 0.5% (w/w) about 20% (w/w) nicotine and an acid precursor in a biologically acceptable liquid carrier; a resistive heater in communication with the reservoir; and an electrical connector configured to form an electrical contact with a controller adapted to apply energy to the resistive heater to vaporize the biologically acceptable liquid carrier into vapor particles comprising: an acid formed by the heat of vaporization from the acid precursor, from about 0.5% (w/w) to about 20% (w/w) protonated nicotine, and the biologically acceptable liquid carrier.

A cartridge device for a vaporizer for delivering protonated nicotine to a user may include: a first reservoir comprising from about 0.5% (w/w) and about 20% (w/w) nicotine in a biologically acceptable liquid carrier; a second reservoir comprising an acid precursor; a first resistive heater in communication with both the first reservoir and the second reservoir; and an electrical connector configured to form an electrical contact with a controller adapted to apply energy to the first resistive heater to vaporize the biologically acceptable liquid carrier and the acid precursor into vapor that includes an acid formed by the heat of vaporization from the acid precursor, from about 0.5% (w/w) to about 20% (w/w) protonated nicotine, and the biologically acceptable liquid carrier.

A cartridge device for a vaporizer for delivering protonated nicotine to a user may include: a first reservoir comprising from about 0.5% (w/w) and about 20% (w/w) nicotine in a biologically acceptable liquid carrier; a second reservoir comprising an acid precursor; a first resistive heater in communication with the first reservoir; a second resistive heater in communication with the second reservoir; and an electrical connector configured to form an electrical contact with a controller adapted to apply energy to the first resistive heater to vaporize the biologically acceptable liquid carrier and nicotine, and to apply energy to the second resistive heater to form vapor particles including an acid formed by the acid precursor; and a chamber or channel wherein the vapor of the biologically acceptable liquid carrier and nicotine combined with the vapor particles including the acid to form a vapor of protonated nicotine including from about 0.5% (w/w) to about 20% (w/w) protonated nicotine, the acid, and the biologically acceptable liquid carrier.

Any of the methods for generating an aerosol and apparatuses for performing these methods may include one or more substrate holding or otherwise retaining the liquid solution (e.g., in a sponge or other porous holder) arranged in the vapor pathway through which one or more components of the final vapor delivered to a user may be eluted into the vapor. For example, nicotine and/or an acid may be eluted into the vapor from a sponge including a liquid solution of the nicotine and/or acid.

For example, described herein are methods of generating an aerosol of protonated nicotine using a vaporizer device that include: vaporizing a first material contained in a first reservoir of the vaporizer device, wherein the first material comprises a biologically acceptable liquid carrier; drawing the vapor through at least one substrate holding the liquid solution comprising one or more of: nicotine and an acid; and emitting a vapor from the vaporization device, wherein the vapor comprises from about 0.5% (w/w) to about 20% (w/w) protonated nicotine, the acid, and the biologically acceptable liquid carrier.

The biologically acceptable liquid carrier may comprise a vegetable glycerol and a glycol. For example, the biologically acceptable liquid carrier in the emitted vapor may comprise from about 90% to about 10% of vegetable glycerol and a glycol.

The final molar ratio of the nicotine to acid in the vapor may be any appropriate molar ratio of nicotine to acid (e.g., between about 0.7:1 and about 1:3, etc.).

In general, any appropriate component may be eluted. These may include nicotine (e.g., freebase nicotine), acid, flavorants, etc. The vapor is typically a vapor of the biologically acceptable liquid carrier. In some variations the vapor includes nicotine and the acid (to form the salt solution) is added to the vapor by elution from a sponge or other liquid carrier holding a liquid solution of acid that is in the vapor pathway (e.g., a draw pathway within the device). For example, the first material may comprise nicotine in the biologically acceptable liquid carrier and the at least one liquid solution may comprise a liquid solution of the acid. Alternatively, the acid may be in the vapor (including an acid formed from an acid precursor as mentioned above) and the nicotine is added to the vapor by passing the vapor through/around a liquid solution (e.g., sponge, droplet, etc.) containing nicotine. For example, the first material may comprise an acid or an acid precursor that forms the acid upon heating in the biologically acceptable liquid carrier and the at least one liquid solution may comprise a liquid solution of nicotine. In some variations, both nicotine and acid are eluted from a solution (e.g., sponge) in the vapor path. For example, the at least one liquid solution may comprise a first liquid solution of nicotine and a second liquid solution of the acid.

In any of these variations, emitting the vapor may comprise emitting a particle size from about 0.1 microns to about 5 microns.

In general, the step of drawing the vapor through the substrate holding the liquid solution may include any step of eluting a component (e.g., nicotine, acid, flavorant, etc.) from a liquid solution into a vapor, including passing the vapor through or adjacent a liquid solution. Porous substrates such as sponges may be used. Such porous substrates may create humid regions formed of the liquid solution. Drawing the vapor through the at least one liquid solution may comprise drawing the vapor through (e.g., around, within, over, etc.) at least one porous substrate holding the liquid solution. The porous substrate may be wetted by the liquid solution, and may still include passages for air. For example, drawing the vapor through the at least one liquid solution may comprise drawing the vapor through a sponge holding the liquid solution. The liquid solution may be warmed, for example, by conduction from the atomizer (e.g., resistive heater), or it may be insulated from heating. Alternatively a separate warming heater may be used. Warming may be below about 100° C.

In general, the method may include vaporizing the first material by heating the first material to between about 100° C. and about 300° C.

For example, described herein are methods of generating an aerosol or protonated nicotine using a vaporizer device, the method comprising: vaporizing a first material contained in a first reservoir of the vaporizer device, wherein the first material comprises nicotine in a biologically acceptable liquid carrier; drawing the vapor through a porous substrate holding a liquid solution comprising an acid; and emitting a vapor from the vaporization device, wherein the vapor comprises from about 0.5% (w/w) to about 20% (w/w) protonated nicotine, the acid, and the biologically acceptable liquid carrier.

A method of generating an aerosol of protonated nicotine using a vaporizer device may include: vaporizing a first material contained in a first reservoir of the vaporizer device, wherein the first material comprises a biologically acceptable liquid carrier and an acid or an acid precursor that forms the acid upon heating; drawing the vapor through a porous substrate holding a liquid solution comprising nicotine; and emitting a vapor from the vaporization device, wherein the vapor comprises from about 0.5% (w/w) to about 20% (w/w) protonated nicotine, the acid, and the biologically acceptable liquid carrier.

A method of generating an aerosol of protonated nicotine using a vaporizer device may include: vaporizing a first material contained in a first reservoir of the vaporizer device, wherein the first material comprises a biologically acceptable liquid carrier; drawing the vapor through a porous substrate holding a liquid solution comprising nicotine and an acid; and emitting a vapor from the vaporization device, wherein the vapor comprises from about 0.5% (w/w) to about 20% (w/w) protonated nicotine, the acid, and the biologically acceptable liquid carrier.

A method of generating an aerosol of protonated nicotine using a vaporizer device may include: vaporizing a first material contained in a first reservoir of the vaporizer device, wherein the first material comprises a biologically acceptable liquid carrier; drawing the vapor through a first porous substrate holding a liquid solution of nicotine; drawing the vapor through a second porous substrate holding a liquid solution of an acid; and emitting a vapor from the vaporization device, wherein the vapor comprises from about 0.5% (w/w) to about 20% (w/w) protonated nicotine, the acid, and the biologically acceptable liquid carrier.

Any of the vaporizer devices described herein may be configured to deliver protonated nicotine to a user by any of these methods, including methods in which the vapor is passed through a substrate holding the liquid solution. For example, a vaporizer device configured to deliver protonated nicotine to a user may include: a reservoir comprising a first liquid solution of a biologically acceptable liquid carrier; a resistive heater in communication with the reservoir and adapted to vaporize the first liquid solution; a draw channel in fluid communication with the resistive heater; a mouthpiece in fluid communication with the draw channel; and a porous substrate within the draw channel holding a second liquid solution comprising one or more of nicotine and an acid, wherein the porous substrate is positioned in the draw channel between the resistive heater and the mouthpiece, so that vapor formed by the resistive heater passes through the second liquid solution.

A vaporizer device for delivering protonated nicotine to a user may include a reservoir comprising a first liquid solution of a biologically acceptable liquid carrier; a resistive heater in communication with the reservoir and adapted to vaporize the first liquid solution; a draw channel in fluid communication with the resistive heater; a mouthpiece in fluid communication with the draw channel; and a porous substrate within the draw channel holding a second liquid solution comprising one or more of nicotine and an acid, wherein the porous substrate is positioned in the draw channel between the resistive heater and the mouthpiece, so that vapor formed by the resistive heater passes through the second liquid solution to form vapor particles comprising from about 0.5% (w/w) to about 20% (w/w) protonated nicotine, the acid, and the biologically acceptable liquid carrier.

A vaporizer device for delivering protonated nicotine to a user may include: a reservoir comprising a first liquid solution of a biologically acceptable liquid carrier; a resistive heater in communication with the reservoir and adapted to vaporize the first liquid solution; a draw channel in fluid communication with the resistive heater; a mouthpiece in fluid communication with the draw channel; a first porous substrate within the draw channel holding a second liquid solution comprising nicotine, wherein the first porous substrate is positioned in the draw channel between the resistive heater and the mouthpiece; and a second porous substrate within the draw channel holding a third liquid solution comprising an acid, wherein second porous substrate is positioned in the draw channel between the first porous substrate and the resistive heater or between the first porous substrate and the mouthpiece.

As mentioned, any of these devices may include a controller configured apply energy to the resistive heater to vaporize the biologically acceptable liquid carrier. For example, the controller may be configured apply energy to the resistive heater to vaporize the biologically acceptable liquid carrier, wherein the controller is configured to cause the resistive heater to heat to between about 100° C. and 300° C.

Any of these devices may be configured as cartridges comprising one or more electrical contacts for connection to a controller configured apply energy to the resistive heater to vaporize the biologically acceptable liquid carrier.

In any of these devices, two or more liquid substrates (e.g., porous substrates such as sponges) may be used. For example the device may include a second porous substrate within the draw channel holding a third liquid solution comprising a component (e.g., an acid, flavorant, etc.). The second porous substrate may be positioned in the draw channel between the first porous substrate and the resistive heater or between the first porous substrate and the mouthpiece.

Any of the apparatuses (devices, systems, etc.) described herein may also include a tobacco material that is not vaporized or burnt, but through which the vapor passes. This may provide a user experience from the vaporization that more closely mimics traditional cigarette smoking. The tobacco may be a tobacco liquid solution (e.g., a tobacco oil, slurry, suspension, etc.) which is held in a liquid substrate as described above, including sponge or other porous substrate. In some variations, tobacco material is warmed or heated. The temperature may be kept below the temperature for vaporization (e.g., below about 130° C., 125° C., 120° C., 110° C., 100° C., etc.) of the tobacco material while the vapor is passed through or around the tobacco material. In some variations the tobacco material is not a liquid solution, but is a solid solution (e.g., dried tobacco, loose-leaf tobacco, etc.).

For example, any of the methods of generating an aerosol or protonated nicotine using a vaporizer device may include:

vaporizing a first material contained in a reservoir of the vaporizer device, wherein the first material comprises a biologically acceptable liquid carrier and forming a vapor of between about 0.5% and 20% protonated nicotine, acid, and the biologically acceptable liquid carrier; drawing the vapor through a tobacco material; and emitting the vapor from the vaporization device.

A method of generating an aerosol or protonated nicotine using a vaporizer device that includes drawing the vapor through a tobacco material may include: vaporizing a first material contained in a reservoir of the vaporizer device, wherein the first material comprises a biologically acceptable liquid carrier and forming a vapor of between about 0.5% and 20% protonated nicotine, acid, and the biologically acceptable liquid carrier; drawing the vapor through a porous substrate holding a tobacco material, wherein the tobacco material is warmed to a temperature that is less than the vaporization temperature of the tobacco material; and emitting the vapor from the vaporization device.

In general, drawing the vapor through a tobacco material may include drawing the vapor thorough a porous substrate (e.g., a substrate having two or more air paths through which the vapor may be passed) that holds the tobacco material, including a liquid material as described above for the more general case. For example, drawing the vapor through a tobacco material may comprise drawing the vapor through a porous substrate comprising the tobacco material.

As mentioned, any of these methods may include warming the tobacco material, such as warming the tobacco material to a temperature that is less than the vaporization temperature for tobacco. For example, warming the tobacco material to a temperature that is less than 125° C. The tobacco material may be conductively heated during vaporization of the first material (e.g., by conducting heat from the atomizer, which may be a resistive heater, etc.).

Any appropriate tobacco material may be used, including (but not limited to): shredded tobacco, an oil of tobacco (tobacco oil), etc.

Any of these methods may be configured for use with a device or cartridge that includes the material being vaporized as well as the tobacco material. For example, the method may include vaporizing by heating a resistive heater of a cartridge housing the reservoir and the tobacco material, wherein the cartridge is in electrical communication with a base housing a controller and a power supply.

Any of the vaporizers described herein may be configured for delivering protonated nicotine to a user and passing the vapor through a substrate holding a tobacco material. For example, a vaporization device may include: a reservoir comprising a first liquid solution of nicotine, a biologically acceptable liquid carrier, and an acid or an acid precursor that forms the acid upon heating; a resistive heater in communication with the reservoir and adapted to vaporize the first liquid solution to form a vapor of between about 0.5% and 20% protonated nicotine, acid, and the biologically acceptable liquid carrier; a draw channel in fluid communication with the resistive heater; a mouthpiece in fluid communication with the draw channel; and a tobacco material positioned in the draw channel between the resistive heater and the mouthpiece, so that vapor formed by the resistive heater passes through the tobacco material.

A vaporizer device for delivering protonated nicotine to a user may include: a reservoir comprising a first liquid solution of nicotine, a biologically acceptable liquid carrier, and an acid or an acid precursor that forms the acid upon heating; a resistive heater in communication with the reservoir and adapted to vaporize the first liquid solution to form a vapor of between about 0.5% and 20% protonated nicotine, acid, and the biologically acceptable liquid carrier; and a draw channel in fluid communication with the resistive heater; a mouthpiece in fluid communication with the draw channel; and a porous substrate within the draw channel holding a tobacco material, wherein the porous substrate is positioned in the draw channel between the resistive heater and the mouthpiece, so that vapor formed by the resistive heater passes through the tobacco material; a thermally conductive region in communication with the tobacco material configured to warm the tobacco material.

As mentioned any of the devices described herein may include a thermally conductive region in communication with the substrate holding the liquid and/or tobacco material through which the vapor is drawn. For example, a thermally conductive region may be coupled to a second heater and configured to warm the tobacco material to a temperature that is less than the vaporization temperature for tobacco. When used with a tobacco material, the thermally conductive region may be coupled to the resistive heater and configured to warm the tobacco material to a temperature that is less than the vaporization temperature for tobacco. For example, the thermally conductive region may be coupled to the resistive heater and configured to warm the tobacco material to a temperature that is less than 125° C.

Any of these devices may include a controller configured apply energy to the resistive heater to vaporize the first liquid solution, wherein the controller is configured to cause the resistive heater to heat to between about 100° C. and 300° C.

Any of these devices may be configured as a cartridge for mating with a base comprising a controller to control the temperature of the resistive heater and a power source, the device comprising an electrical connector for electrically connecting the resistive heater and the controller.

In some aspects, a method, apparatus, computer program product, and/or system are provided. In an implementation, a method for aerosolization of compartmentalized materials is provided. The method can include vaporizing, by a heater, at least a portion of a first material to form a first vapor, wherein the first material is stored in a reservoir coupled to the heater. The method can further comprise providing, through a draw channel comprising the heater, the first vapor to a second material within the draw channel, wherein the second material comprises one or more of nicotine and an acid, wherein the second material is positioned between the resistive heater and an exit point of the draw channel. The method can also include forming, based on the first vapor passing through and/or around the second material, an inhalable vapor. The system can include (or otherwise utilize) at least one processor and/or memory, which can be configured to perform at least a portion of the steps of the method.

In some variations, the first material comprises about 10-90% vegetable glycerol, where the rest (or at least a portion of the rest) comprises another glycol, such as propylene glycol, and/or a flavorant. In some aspects, a controller is utilized to apply energy to the heater to vaporize the first material. In some implementations, the controller is configured to cause the heater to heat to between about 100° C. and about 300° C.

In some implementations, the components utilized for the method are comprised in an apparatus, which comprises and/or is comprised in a cartridge having one or more electrical contacts for connection to a controller, wherein the controller is configured to apply energy to the heater to vaporize the first material. In some aspects, the inhalable vapor is formed based elution of at least a portion of the second material. In some variations, the second material comprises and/or is comprised in at least one of a porous substrate or a sponge. In other variations, the second material comprises and/or is comprised in at least one of tobacco or a botanical.

In some variations, the second material comprises nicotine and the first material comprises an acid or an acid precursor that forms the acid upon heating. In various implementations, the second material comprises an acid and the first material comprises between 0.5% and 20% nicotine. In some aspects, the inhalable vapor includes particles comprising from about 0.5% (w/w) to about 20% (w/w) protonated nicotine, acid, and carrier material. In various aspects, the inhalable vapor comprises a nicotine aerosol.

In some variations, a third material may also exist within the draw channel, wherein the third material comprises an acid, wherein the second material comprises nicotine, and/or wherein the third material is positioned in the draw channel between the heater and the exit point. In some aspects, the third material comprises and/or is comprised in at least one of a porous substrate or a sponge. In some variations, a mouthpiece (e.g., something as simple as a flat surface with a hole) is coupled to the exit point and/or configured to allow for passage of the inhalable vapor for inhalation by a user.

As used herein, the first material, the second material, and/or the like can include one or more of a solid material (e.g., a singular element or a compound in a solid form), a liquid (e.g., a singular element or a compound in a liquid form), and/or a gas (e.g., a singular element or a compound in a gaseous form). For example, in some aspects, the second material can comprise tobacco or some other botanical which has been soaked (or otherwise placed in contact with) a liquid flavorant.

Implementations of the current subject matter can include systems and methods consistent with the present description, including one or more features as described, as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 10 illustrates one variation of a dual tank/heater assembly which may be part of an electronic cigarette or a cartridge for an electronic cigarette, in accordance with some example implementations; and FIG. 11 illustrates another variation of a dual tank/heater assembly which may be part of an electronic cigarette or a cartridge for an electronic cigarette, in accordance with some example implementations.

When practical, similar reference numbers denote similar structures, features, or elements.

DETAILED DESCRIPTION

Figure 1:
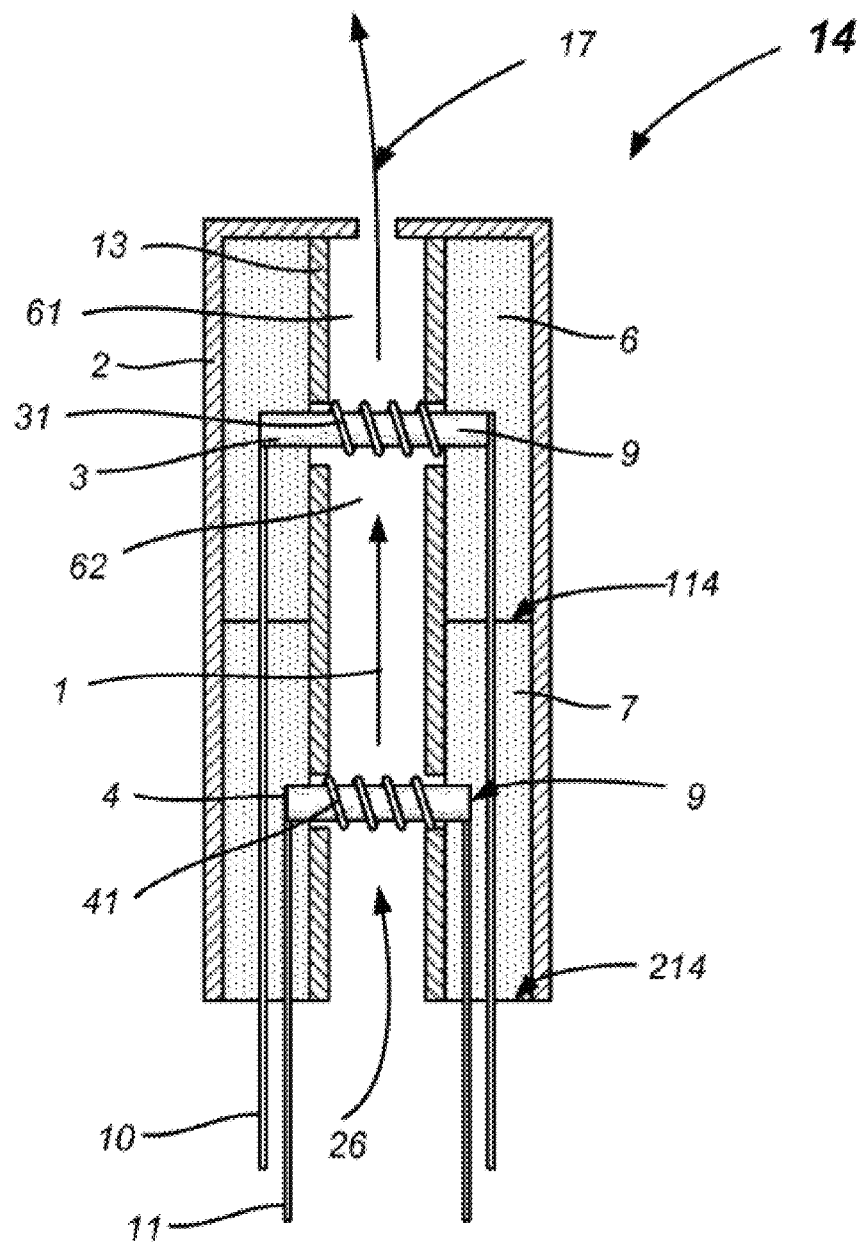
FIG. 1 shows a sectional view of a detachable cartridge having a first heating element, a second heating element, a first compartment for containment of vaporizable material, and a second compartment for containment of vaporizable material, in accordance with some example implementations.

The vaporization apparatuses (e.g., devices, systems and compositions) and methods described herein include methods and apparatuses in which one or more chemical components of the aerosol vapor to be delivered to a user is stored and/or processed separately, including separately vaporized, and/or combined with the other components of the final composition of the vapor. In particular, described herein are vapors of protonated nicotine that include nicotine and an acid (resulting in a nicotine salt in solution) in a biologically acceptable liquid carrier. Additional components such as flavorants, buffers, or the like may be included. Thus, many of the methods and apparatuses described herein include separate storage compartments for one or more of these components (e.g., carrier, nicotine, acid, etc.) and/or forming a vapor including some, but not all, of these components (e.g., excluding nicotine and/or acid) and adding them after forming the vapor. Also described herein are method and apparatuses for enhancing the user experience (taste, aroma, etc.) by treating the vapor with a tobacco material.

The apparatuses and methods generally describe forming a vapor from a material. In some variations the vapor is formed (e.g., from the carrier), and modified to include a nicotine salt (e.g., nicotine and an appropriate acid). The vapor may be delivered for inhalation by a user by a vaporization device. The vaporization device may be a handheld vaporization device. The vaporization device may be held in one hand by the user.

The vaporization device may comprise one or more atomizers, which may be heating elements, including resistive heating elements. The heating element may heat the material such that the temperature of the material increases. Vapor may be generated as a result of heating the material. Energy may be required to operate the heating element, the energy may be derived from a battery in electrical communication with the heating element. Alternatively a chemical reaction (e.g., combustion or other exothermic reaction) may provide energy to the heating element.

One or more aspects of the vaporization device may be designed and/or controlled in order to deliver a vapor with one or more specified properties to the user. For example, aspects of the vaporization device that may be designed and/or controlled to deliver the vapor with specified properties may comprise the heating temperature, heating mechanism, device air inlets, internal volume of the device, and/or composition of the material.

In some cases, a vaporization device may have an "atomizer" or "cartomizer" configured to heat an aerosol forming solution (e.g., vaporizable material). The aerosol forming solution may typically include a biologically acceptable liquid carrier, such as a mixture of glycerin (e.g., vegetable glycerin) and/or propylene glycol. The vaporizable material may be heated to a sufficient temperature such that it may vaporize (e.g., between 100° C. and 300° C.). The apparatus or method may include one or more pre-set vaporization temperatures and the apparatus or method may control (via controller including feedback logic) the temperature to a predetermined and/or selected temperature.

An atomizer may comprise a small heating element configured to heat and/or vaporize at least a portion of the vaporizable material and a wicking material that may draw a liquid vaporizable material in to the atomizer (e.g., heater). In some aspects, the drawing of the liquid vaporizable material can be drawn by the wick and/or into the atomizer via capillary action. When the apparatus includes a wicking material, the wicking material may comprise silica fibers, cotton, ceramic, hemp, stainless steel mesh, and/or rope cables. The wicking material may be configured to draw the liquid vaporizable material in to the atomizer without a pump or other mechanical moving part. A resistance wire may be wrapped around the wicking material and then connected to a positive and negative pole of a current source (e.g., energy source). The resistance wire may be a coil. When the resistance wire is activated the resistance wire (or coil) may have a temperature increase as a result of the current flowing through the resistive wire to generate heat. The heat may be transferred to at least a portion of the vaporizable material through conductive, convective, and/or radiative heat transfer such that at least a portion of the vaporizable material vaporizes.

Alternatively or in addition to the atomizer, the vaporization device may be configured as a "cartomizer" to generate an aerosol from the vaporizable material for inhalation by the user. The cartomizer may comprise a cartridge and an atomizer. The cartomizer may comprise a heating element surrounded by a liquid-soaked poly-foam that acts as holder for the vaporizable material (e.g., the liquid). The cartomizer may be reusable, rebuildable, refillable, and/or disposable. The cartomizer may be used with a tank for extra storage of a vaporizable material.

Air may be drawn into the vaporization device to carry the vaporized aerosol away from the heating element, where it then cools and condenses to form liquid particles suspended in air, which may then be drawn out of the mouthpiece by the user. For example, any of the apparatuses described herein may include a draw channel or passage. The draw channel may be in fluid communication with the heater so that vapor formed by the heater passes into the draw channel, which is also in fluid communication with the mouthpiece, which may be integrated with the device (including a cartridge).

The vaporization of at least a portion of the vaporizable material (e.g., biologically acceptable liquid carrier) may occur at lower temperatures in the vaporization device compared to temperatures required to generate an inhalable vapor in a cigarette. A cigarette may be a device in which a smokable material is burned to generate an inhalable vapor. The lower temperature of the vaporization device may result in less decomposition and/or reaction of the vaporized material, and therefore produce an aerosol with many fewer chemical components compared to a cigarette. In some cases, the vaporization device may generate an aerosol with fewer chemical components that may be harmful to human health compared to a cigarette. Additionally, the vaporization device aerosol particles may undergo nearly complete evaporation in the heating process, the nearly complete evaporation may yield an average particle size (e.g., diameter) value that may be smaller than the average particle size in tobacco or botanical based effluent. The vaporization device may operate at a temperature at or below about 300° C.

The term "aerosol" may generally refer to a colloid of fine solid particles or liquid droplets in air or another gas. In general, the aerosols described herein are liquid aerosols of primarily about 80% or greater, about 85% or greater, about 90% or greater, or about 95% or greater liquid particles in air. The liquid or solid particles in an aerosol may have varying diameters of average mass that may range from monodisperse aerosols, producible in the laboratory, and containing particles of uniform size; to polydisperse colloidal systems, exhibiting a range of particle sizes. As the sizes of these particles become larger, they have a greater settling speed which causes them to settle out of the aerosol faster, making the appearance of the aerosol less dense and to shorten the time in which the aerosol will linger in air. Interestingly, an aerosol with smaller particles will appear thicker or denser because it has more particles. Particle number has a much bigger impact on light scattering than particle size (at least for the considered ranges of particle size), thus allowing for a vapor cloud with many more smaller particles to appear denser than a cloud having fewer, but larger particle sizes.

A vapor may generally refer to a substance in the gas phase at a temperature lower than its critical point. As used herein, a vapor may include a liquid aerosol; for convenience the term vapor and aerosol, which may generally refer to liquid aerosols, may be used interchangeably herein, as is common in the art of electronic vaporization devices.

As used herein the term "humectant" may generally refer to as a substance that is used to keep things moist. A humectant may attract and retain moisture in the air by absorption, allowing the water to be used by other substances. The carriers (biologically acceptable liquid carriers) may include humectants. Examples may include or more of (e.g., mixtures of): propylene glycol, sugar polyols such as glycerol, glycerin, and honey.

The methods and apparatuses described herein have a wide range of applications for inhalation of an active substance, and particularly nicotine. As mentioned above, although the examples described herein focus on nicotine, the devices, systems, kits and methods described herein could be used, for example, to vaporize any substance, such as a botanical, pharmaceutical, nutraceutical, or any other substance for inhalation to provide a benefit or sensation to an end user.

For example, described herein are devices for generating an inhalable aerosol ("vapor") that may be or include a detachable cartridge having one or more heating elements, a first compartment for containment of first vaporizable material, and a second compartment for containment of a second vaporizable material, wherein the first and second vaporizable material are typically different. A vaporizer for use with the cartridge may include a separate body having a battery and circuitry for controlling the device wherein the cartridge and body may be coupled by an electrical and/or mechanical connector (or two or more electrical and/or mechanical connectors). Also described herein are integrated devices.

For example, a detachable cartridge may comprise two or more compartments with at least one compartment having at least one heating element and at least one vaporizable material. The device may be configured such that each compartment containing at least one resistive heating element also comprises a wicking material that is in direct contact with the vaporizable material in the compartment. At least one heating element in at least one compartment may be exposed to an air passage in the cartridge.

At least one resistive heater in the cartridge may be designed to reach a closely controlled target temperature, below the pyrolytic temperature of tobacco, and more specifically, a target "vapor temperature", greater than about 100° C., but less than about 300° C., intended to convert the vaporizable material of at least one compartment to a visible vapor, such as about 170° C. for flavorants, about 190° C. for nicotine, and about 210° C. for humectants.

In some embodiments, at least one resistive heater comprises a wire coil wrapped around a wicking material (e.g., silica) that penetrates a moisture resistant liquid barrier of at least one compartment holding the vaporizable material and allows the vaporizable material to "wick" around the wire and be heated to a controlled temperature when activated. This occurs when the ends of wires traversing the length of the cartridge, exiting the compartment distally and connecting to the body, are activated by a mechanism, optionally a button mechanism, and circuitry connected to the battery in the body. Additionally, different wicking rates of the vaporizable material in the compartment is obtained using different wick materials and/or different arrangements of the heating element and the wick (e.g., heating element wrapped around the wick, heating element passing through the wick). Wicking materials at least comprise silica, cotton, stainless steel mesh, and Ekowool. Wicking properties, which effect wicking rates, include wicking material density, composition, dimension, shape, size, length, width, among others.

In some embodiments having two or more heating elements, wicking material of the first heating element is the same or different than the wicking material of the second heating element. Heating element material properties include heating element material composition, density, dimension, shape, size, length, width, among others. In some embodiments, the wicking material of the first heating element is the same as the wicking material of the second heating element and the wicking rate of the vaporizable material in the first compartment to at least one heating element is the same or different as the wicking rate of the vaporizable material in the second compartment to at least one heating element. In some embodiments, the wicking material of the first heating element is different than the wicking material of the second heating element, and the wicking rate of the vaporizable material in the first compartment to at least one heating element is the same or different as the wicking rate of the vaporizable material in the second compartment to at least one heating element.

In embodiments having two or more heating elements (e.g., two or more resistive heaters) the target temperature for the first heating element is the same or different as the target temperature for the second heating element. In some embodiments, the vaporizable material in a first compartment is different than a vaporizable material in the second compartment, and the target temperature for the first heating element may be the same or different as the target temperature for the second heating element. Target temperatures at least comprise temperatures below the pyrolytic temperature of tobacco, greater than about 100° C. but less than about 300° C., about 170° C. for flavorants, about 190° C. for nicotine, about 210° C. for humectants, about 100° C., about 120° C., about 140° C., about 160° C., about 180° C., about 200° C., about 220° C., about 240° C., about 260° C., about 280° C., and about 300° C.

In some embodiments, resistive heater elements are used as the heating elements and may be positioned within at least one compartment for containment of vaporizable material are "breath-activated" when the user puffs on the device. This activation mode may be accomplished by vacuum activated contact switches (e.g., pressure-activated sensors), and/or solid state pressure sensors and circuitry connected to the battery in the attachable body.

In some variations at least one resistive heater element within at least one compartment for containment of vaporizable material is selectively activated when the user picks up the device. This activation mode may be accomplished by a button mechanism, an accelerometer, and/or solid state sensors and circuitry connected to the battery in the attachable body. The selective activation cycle has several modes including but not limited to a "preheat" setting for the resistive heaters that brings the temperature of at least one resistive heater up to a "pre-vaporization" temperature (e.g.: 100°-130° C.); a sleep mode where the device deactivates and shuts down after a short period of time; or an "off" mode when no use or movement is detected for a longer period of time, or the user manual changes the mode and/or deactivates the device with the button.

A resistive heater may include a resistive heater wire that is inserted through, surrounds, or is surrounded by wicking material in direct contact with one of the compartments containing vaporizable material. The ends of wires traverse the length and exit the compartment distally where they attach to a first connection mechanism in the distal end of the cartridge that matches a second connection mechanism on the body.

In some embodiments, the device is configured as or includes a detachable cartridge that may be a single-unit construction wherein the entire cartridge with all of its components, are replaced en masse. A detachable cartridge may have a modular construction wherein the first and/or second compartments containing component vaporizable materials and a heater, or combinations of two or more compartments, each containing different component vaporizable material (and at least some of them a heater), are removable. In some embodiments, the individual compartments and heaters are arranged in a stacked-series configuration, a parallel configuration, a concentric configuration, or any combination of series-stacked, parallel or concentric configuration within the detachable cartridge.

In some embodiments, the individual compartments containing the component vaporizable materials and heaters within a cartridge are removable and replaceable. In still other embodiments the individual compartments containing the component vaporizable materials and heaters within the cartridge are interchangeable with replacement components. In some embodiments, the individual compartments containing the vaporizable materials and heaters within the cartridge are recyclable and reusable and is refilled by the user.

As used herein a reservoir may be a compartment, and may include a sponge or substrate holding a liquid, as will be described in greater detail below. When a substrate (e.g., porous substrate such as a sponge) holding a liquid is used, it may be connected to a supply reservoir holding the liquid that can replenish the liquid in the substrate.

In some embodiments, the device may comprise different mechanical and/or electrical connection mechanisms between a detachable cartridge and a reusable body portion. Examples of mechanical connections may include: a threaded connection, a tapered connection, a magnetic connection, a spring-loaded connection, a spring detent connection, a snap-fit connection, a compression connection, or any combination thereof.

In some embodiments, the reusable body portion also comprises at least one push button for operator control of the circuitry. In some embodiments, the body also comprises at least one LED indicator to apprise the user of a functional operation of the device.

In some embodiments the battery is not rechargeable. In some embodiments the battery is rechargeable. In some embodiments the battery is a lithium-based rechargeable battery. In some embodiments the attachable body comprises a mechanism for recharging the battery.

In some embodiments the device is configured to further comprise a detachable mouthpiece, wherein the mouthpiece is the detachable cartridge. In some embodiments the mouthpiece has at least one air passage (e.g., draw channel) therethrough and at least one heating element is exposed to the air passage. The draw channel may include regions or sub-regions where vapors having different components my recombine. In some variations the draw channel may include one or more porous substrates with a liquid including a component material (e.g., nicotine, acid, flavorant, tobacco, etc.).

In some embodiments the detachable mouthpiece cartridge is a single-unit, non-modular construction. In some embodiments the compartments for containment of vaporizable material are aligned in series within the detachable mouthpiece cartridge, are aligned in parallel within the detachable mouthpiece cartridge, are aligned concentrically within the detachable mouthpiece cartridge, and/or are aligned in any combination of series stacking, concentric, and parallel alignment within the detachable mouthpiece cartridge.

Figure 4:
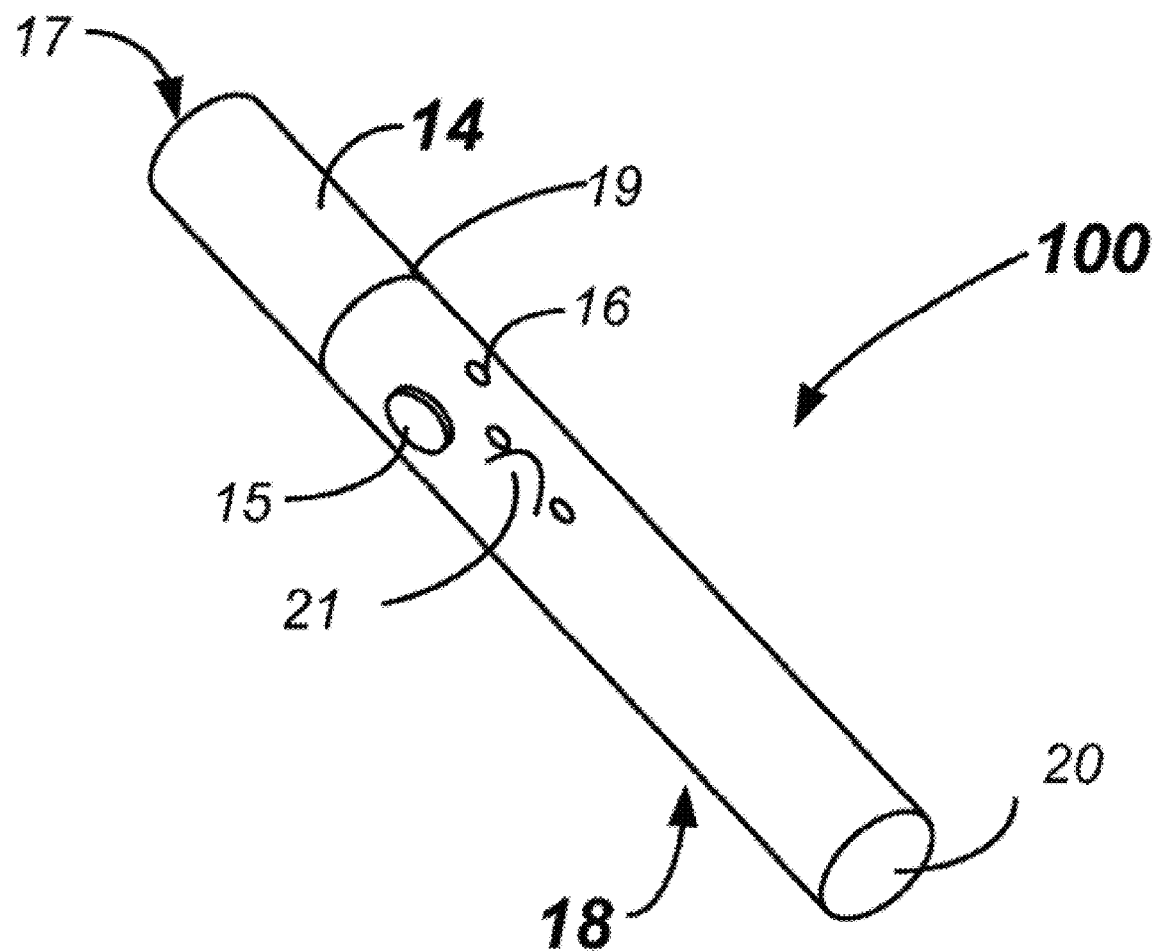
FIG. 4 illustrates an isometric representation of a vaporizer device with dimensions and aspect ratio similar to a conventional cigarette, in accordance with some example implementations.

Provided herein is a device for generating an inhalable aerosol comprising; a detachable cartridge having a first heating element, a second heating element, a first compartment for containment of vaporizable material (such as a biologically acceptable liquid carrier and nicotine), and a second compartment for containment of a second vaporizable material (such as the same or a different carrier and an acid of precursor of an acid), and an attachable body having a battery and circuitry for controlling the device wherein the detachable cartridge and body are coupled by a first connection mechanism. An exemplary device 100 is illustrated in FIG. 4 comprising a detachable cartridge 14, having an air outlet 17, internal compartments for containment of vaporizable material (not shown), heating elements (not shown), at least one air inlet (not shown), and a first connection mechanism 19. Also included is a body 18 comprising an activation button 15, an air inlet 16, a second connection mechanism 19, an optional glow indicator LED 20, a mode indicator LED 21, an internal battery (not shown), an optional accelerometer (not shown), and internal circuit board and circuitry (not shown). In some embodiments a detachable mouthpiece comprises the cartridge 14. In some embodiments a detachable mouthpiece is the cartridge 14.

As shown in FIG. 4, the halves of the exemplary device form a separable, but firm connection 19 and resemble a typical cigarette in appearance. The connection mechanism 19, also interchangeably referred to as an attachment mechanism, is achieved in numerous ways that may include, a threaded connection, a tapered connection, a magnetic connection, a spring-loaded connection, a spring detent connection, a snap-fit connection, a compression connection, or any combination thereof. In some instances, the device 100 is manufactured as a single-use inseparable outer body. In some embodiments, the single button interface 15 provides the mechanism for on, off and wake from sleep. Alternatively, an accelerometer may provide the mechanism for on, off and wake from sleep. In some embodiments, the single button interface also provides the mechanism for selection of specific heater activation within the cartridge. In some embodiments additional buttons are included for any of these functions. For example, pressing the single button for 1 second turns the device on. Continuing to hold the button for 5 seconds disables the motion-based low power standby and automatic shut-down. Alternatively, a second button is used to disable the motion-based low power standby and and/or shut-down. In some embodiments, upon power-up, if the single button is depressed for a very long period (>10 seconds), the device turns off again. This is to prevent inadvertent activation while in a purse, pocket, etc. While on, pressing the button momentarily turns it off. In some embodiments, a single or more than one button could report battery level (via LED blinks, for instance), change operating temperature of the device, or change the nominal intensity of the LED(s)—if the user is in a dark environment and does not want the light to be distracting. These various features could be triggered with one or more buttons or with the same button by pressing it for a prescribed duration or number of presses.

The devices described herein for generating an inhalable aerosol may include a detachable cartridge having a first heating element, a second heating element, a first compartment for containment of a first component vaporizable material, and a second compartment for containment of a second component vaporizable material, wherein the first and second vaporizable materials may be different and may include different component materials, such as nicotine and an acid. These devices may optionally include a body having a battery, at least one activation button, and circuitry for controlling the device, and a first capacitive sensor coupled to the circuitry. In some embodiments, a surface or shell of the device triggers the first capacitive sensor upon a user input to the surface or shell of the device. In some embodiments, a capacitive sensing surface of the first capacitive sensor detects when a user is holding the device, causing the device to indicate that the device is in use or a ready state. In some embodiments, the circuitry causes the heating elements to enter a pre-heat state upon activation or triggering of the first capacitive sensor. In some embodiments, the device exits the pre-heat state or turns off when the first capacitive sensor no longer detects movement of the device. In some embodiments, a surface of the device comprises two electrically isolated capacitive sensing zones wherein the first zone comprises a first capacitive sensor, and the second zone comprises a second capacitive sensor. In some embodiments, when a user contacts a first zone, the device indicates to the user that the device is in use or in a ready state. In some embodiments, the device indicates use or ready state by displaying a pattern of one or more LED(s), displaying a predetermined color of one or more LED(s), or provides an audio signal. In some embodiments, the zones are configured such that when a user touches one of the zones in a predetermined pattern of one or more touches, the device displays a charge level of the battery with a pattern of one or more LED(s) or with a color of one or more LED(s), or with an audio signal. In some embodiments, the zones are configured such that when a user swipes a finger from the first zone to the second zone, or from the second zone to the first zone, the device displays a charge level of the battery with a pattern of one or more LED(s) or with a color of one or more LED(s), or with an audio signal. In some embodiments the device is configured to further comprise a detachable mouthpiece, wherein the mouthpiece is the detachable cartridge. In some embodiments the mouthpiece has at least one air passage therethrough and at least one heating element is exposed to the air passage. In some embodiments the detachable mouthpiece cartridge is a single-unit, non-modular construction. In some embodiments the compartments for containment of vaporizable material are aligned in series within the detachable mouthpiece cartridge, are aligned in parallel within the detachable mouthpiece cartridge, are aligned concentrically within the detachable mouthpiece cartridge, and/or are aligned in any combination of series stacking, concentric, and parallel alignment within the detachable mouthpiece cartridge. In some embodiments, touching the device to lips of a user activates a second capacitive sensor coupled to the circuitry whereby the device heating elements enter a pre-heat state. In some embodiments, when the user inhales the heating elements get fully activated and generate aerosol that is deliverable to the user by such inhalation or by additional inhalation. In some embodiments, inhalation activates a pressure switch to fully activate the heater elements. In some embodiments, the device comprises a button or touch sensor that when pushed or touched, fully activates the heater elements and generates aerosol that is deliverable to a user by inhalation thereby.

FIG. 1 illustrates one example of a detachable cartridge 14 comprising a shell or outer housing 2, having a single central airpath 1 (draw passage) therethrough with an air inlet 26 and air outlet, 17, and a first and second stacked compartments 114, 214, respectively, each surrounded by a liquid barrier 13, and filled with an absorbent batting material 6, 7 that will absorb and hold a first and second vaporizable material. The vaporizable materials in the stacked compartments 114, 214 can be the same or different. Also within each cartridge, and centered within the central airpath are a first and second resistive heater element 3, 4, respectively. One exemplary design of these resistive heater elements 3, 4 include wire coils 31, 41 wrapped around a silica wick 9. The wire coils 31, 41 are coupled to heater circuit wires 10, 11 (alternatively called heater wires herein), which deliver energy to the coils 31, 41 which results in the coils heating up and aerosolizing the liquid vaporizable material wicked by the wicking material 9 from their respective compartments 114 or 214. While the wires 10, 11 are described herein as being coupled to coils 31, 41, other designs of these heating elements are contemplated herein which would be obvious to one of ordinary skill in the art upon reading the disclosure herein. Further, other wick materials are envisioned and must be capable of withstanding the target temperatures generated by the resistive heating element, without changing the flavor of the vapor or imparting an undesirable taste to the end user. The wicking material 9, extends through the inner liquid barrier walls 13, along with the heater circuit wires 10, 11 for the resistive heater elements 3, 4. This provides a steady and even flow of liquid vaporizable material to the resistive heater elements 3, 4 until the vaporizable material within at least one compartment is exhausted. Immediately proximal to each heater element 3, 4, and in the central airpath, is an atomizing chamber 61, 62 where the vapor generated from the heating element will form and mix with inlet air and the vapors formed from any previous heating elements in the airpath 1. In addition, the heater element circuit wires 10, 11 may extend either through, or alongside of, adjacent compartments 114, 214 until they reach the first connection mechanism (not shown) at the distal end of the detachable cartridge 14. The wires then couple to the circuitry of the device which controls the activation and other features of the heater elements, and thus control the timing, delivery, contents, and amount, at least, of the vapor or aerosol deliverable to the user. In some embodiments a detachable mouthpiece comprises the cartridge 14. In some embodiments a detachable mouthpiece is the cartridge 14.

Figure 2:
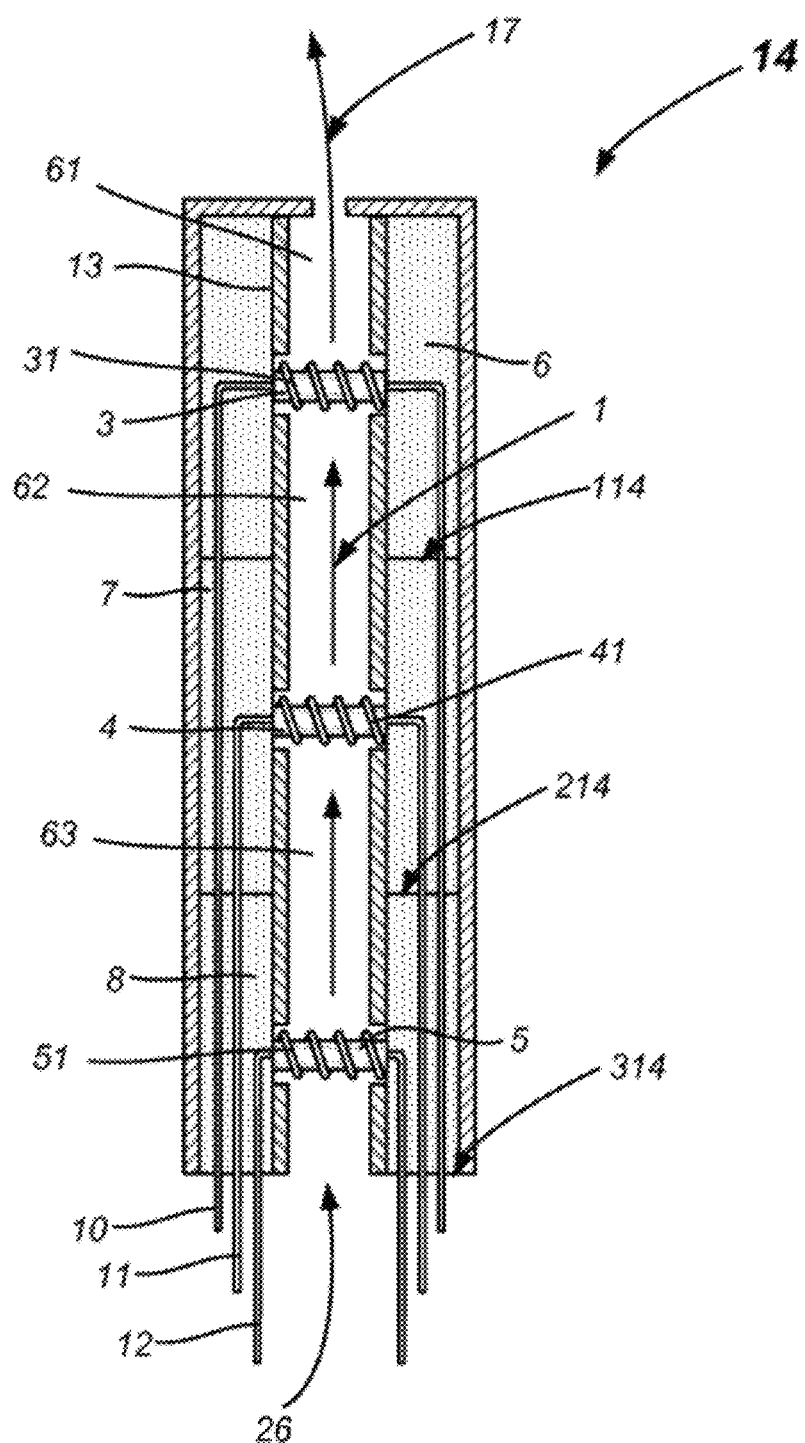
FIG. 2 illustrates a sectional view of a detachable cartridge having a first heating element, a second heating element, a third heating element, a first compartment for containment of vaporizable material, a second compartment for containment of vaporizable material, and a third compartment for containment of vaporizable material, in accordance with some example implementations.

In some embodiments of the detachable cartridge 14, as shown in FIG. 2, the cartridge 14 comprises a shell or outer housing 2, having a single central airpath 1 therethrough, a first, second and third stacked compartments 114, 214, and 314, respectively, each surrounded by a liquid barrier 13, and filled with an absorbent batting material 6, 7, and 8 that will absorb and hold a first, second and third vaporizable material. The vaporizable material in the first, second and third compartments is the same or different. Also within each cartridge, and centered within the central airpath is a first, second, and third resistive heater element 3, 4, and 5, respectively. As described previously, an exemplary design of these resistive heater elements 3, 4, and 5 include wire coils 31, 41, and 51 wrapped around a silica wick 9. The wicking material 9, extends through the inner liquid barrier walls 13, along with the circuit wires 10, 11, and 12 for the resistive heater elements 3, 4 and 5. This provides a steady and even flow of liquid vaporizable material to the resistive heater elements 3, 4 and 5 until the vaporizable material within at least one compartment 114, 214, 314 is exhausted. Immediately proximal to each heater coil 31, 41, and 51, and in the central airpath, is an atomizing chamber 61, 62 and 63 where the vapor generated from the heating element will form and mix with inlet air and the vapors formed from any previous heating elements in the airpath 1. In addition, the heater element circuit wires 10, 11, and 12 may extend either through, or alongside of, adjacent compartments 114, 214, and 314 until they reach the first connection mechanism (not shown) at the distal end of the detachable cartridge 14. In some embodiments a detachable mouthpiece comprises the cartridge 14. In some embodiments a detachable mouthpiece is the cartridge 14.

Figure 3:
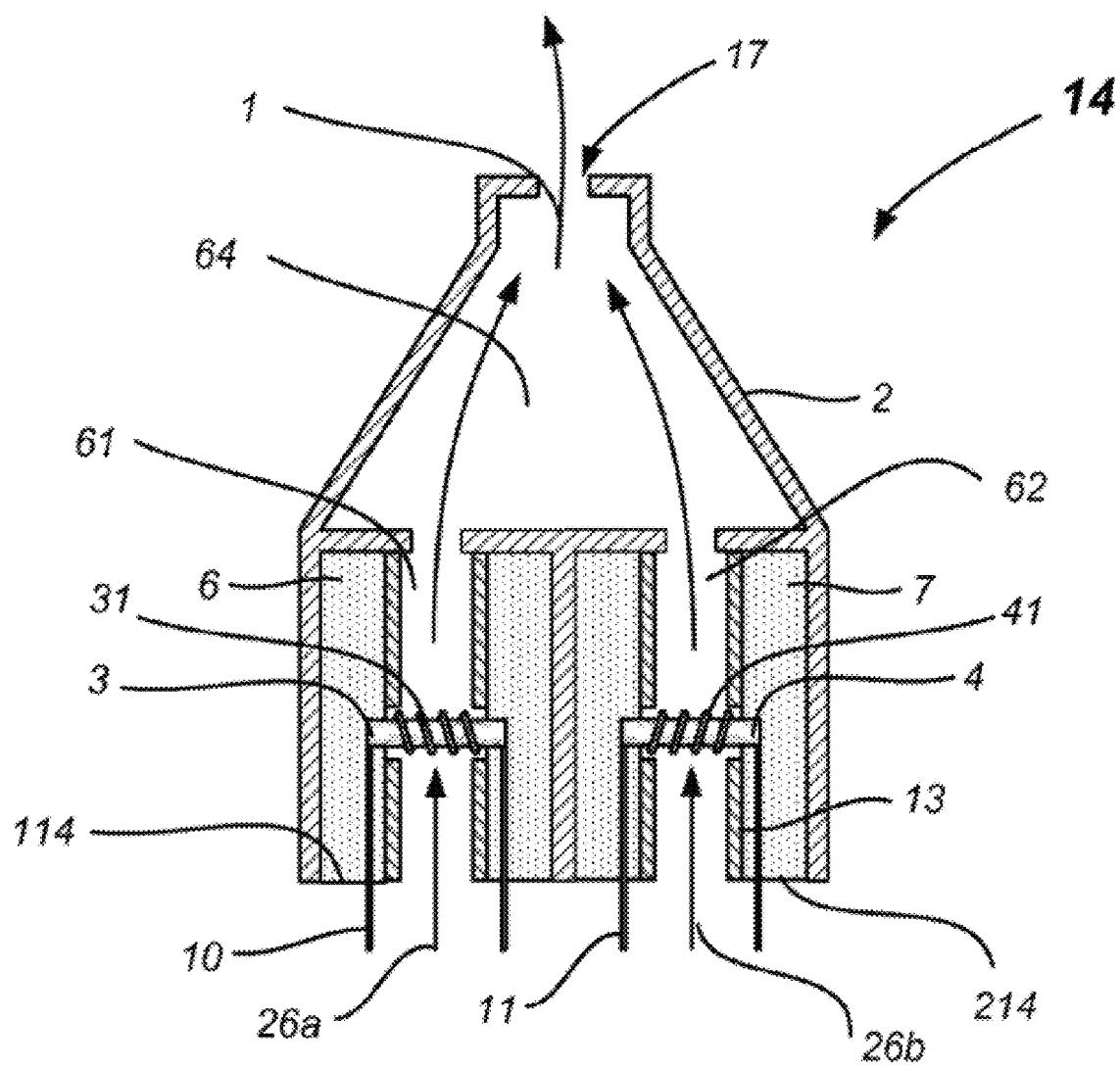
FIG. 3 illustrates a sectional view of a detachable cartridge having two heating elements and two compartments for containment of vaporizable material in a parallel or concentric configuration, in accordance with some example implementations.

Still further, an additional exemplary illustration of the detachable cartridge 14 as shown in FIG. 3 comprises a shell or outer housing 2, having two or more air inlets 26*a*, 26*b*, etc., and compartments, ultimately culminating into a single central airpath 1 at the air outlet, 17. The illustrative embodiment comprises two parallel or circumferentially located compartments 114, 214, respectively, however, one skilled in the art will recognize that there may be two or more circumferentially-located compartments; (e.g.: 3, 4, 5, etc.). The vaporizable material in the first and second compartments can be the same or different. The vaporizable material in two or more compartments can be the same or different. In some embodiments a detachable mouthpiece comprises the cartridge 14. In some embodiments a detachable mouthpiece can include or be part of the cartridge 14.

The illustrative embodiment in FIG. 3 comprises two parallel or circumferentially located compartments 114, 214, each surrounded by a liquid barrier 13, and filled with an absorbent batting material 6, 7 that will absorb and hold a first and second vaporizable material. Also within each cartridge, and centered within the respective airpaths 26*a*, 26*b* is a first and second resistive heater element 3, 4. As described previously, the exemplary design of these resistive heater elements 3, 4 include wire coils 31, 41 wrapped around a silica wick 9. The wicking material 9 extends through the inner liquid barrier walls 13, along with the circuit wires 10, 11 for the resistive heater elements 3, 4. This provides a steady and even flow of liquid vaporizable material to the resistive heater elements 3, 4 until the vaporizable material within at least one compartment 114, 214 is exhausted. Immediately proximal to each coil 31, 41, and in the respective airpath, is an atomizing chamber 61, 62 where the vapor generated from the heating element will form and mix with inlet air from the air inlets 26*a*, 26*b*. Ultimately, the airpaths converge into a central atomizing chamber 64 within a single airpath 1, where the vapors mix before exiting through the air outlet 17. In addition, the heater element circuit wires 10, 11 extend through or alongside of adjacent compartments 114, 214 until they reach the first connection mechanism (not shown) at the distal end of the detachable cartridge 14. In some embodiments a detachable mouthpiece comprises the cartridge 14. In some embodiments a detachable mouthpiece is the cartridge 14.

Any combination of cartridge and heater element circuit arrangement as described herein would be possible for alternative cartridge embodiments. Any combination of mouthpiece, cartridge and heater element circuit arrangement as described herein would be possible for alternative mouthpiece and/or cartridge embodiments.

Provided herein is a device 100 as shown in FIGS. 1, 2, and 3 for generating an inhalable aerosol comprising; a removable cartridge 14 having a proximal end and a distal end, wherein, the removable cartridge 14 comprises; an outer shell 2, a first connection mechanism 19 at the distal end, at least one air inlet in the distal end 26, a first heating element 3 with circuitry 10, a second heating element with circuitry 11, a first compartment containment of vaporizable material 114, a second compartment containment of vaporizable material 214, wherein the vaporizable material in the first compartment 114 is the same or different as the vaporizable material in the second compartment 214, at least one airpath 1 therethrough having exposure to at least one compartment for containment of vaporizable material 114, 214 and at least one heating element 3, 4, comprising heating coils 31, 41, a liquid barrier 13 to isolate the vaporizable materials within at least one compartment and from at least one airpath, an air outlet 17 at the proximal end; and a body 18 having a proximal end and a distal end, coupleable to the cartridge with a second connection mechanism 19; wherein, the body comprises; an outer shell 2, the second connection mechanism 19 at the proximal end, an air inlet in the outer shell 16, at least one indicator light or mode indicator LED 20, 21, a battery 70, circuitry 80, 90 for controlling the device, at least one operator-controlled push-button 15 connected to the circuitry through the outer shell, and an air outlet 27 in the proximal end. In some embodiments a detachable mouthpiece comprises the cartridge 14. In some embodiments a detachable mouthpiece is the cartridge 14.

In some embodiments, the device for generating an inhalable aerosol is an electronic cigarette 100. In some embodiments, the device for generating an inhalable aerosol is an electronic cigar (not shown). In some embodiments, the device for generating an inhalable aerosol is an electronic pipe (not shown). In some embodiments, the device for generating an inhalable aerosol is an electronic water-cooled smoking apparatus (not shown).

Still further, the removable cartridge 14 comprises at least one atomizing chamber 61, 62, 63, 64 adjacent and proximal to the resistive heating elements 3, 4, 5 and heater coils 31, 41, 51. In some embodiments a detachable mouthpiece comprises the cartridge 14. In some embodiments a detachable mouthpiece is the cartridge 14.

In some embodiments, the vaporizable material is a liquid, a gel, a viscous material, a temperature sensitive mesophase material.

In some embodiments of the device, the compartments for containment of component vaporizable material contain nicotine, flavorants, humectants, acid, acid precursor, or water.

In some embodiments of the device, the compartments for containment of component vaporizable material 114, 214, 314 with individual resistive heating elements 3, 4, 5, respectively, are prefilled with the same or different vaporizable material. In some embodiments of the device, the compartments for containment of vaporizable material 114, 214, 314, with individual resistive heating elements 3, 4, 5, respectively, is filled by the user with the same or different vaporizable material. In some embodiments of the device, the compartments for containment of vaporizable material 114, 214, 314, with individual resistive heating elements 3, 4, 5, respectively, are recyclable and/or reusable.

In some embodiments of the device, a mouthpiece comprises the compartments for containment of vaporizable material 114, 214, 314 with individual resistive heating elements 3, 4, 5, respectively, are prefilled with the same or different vaporizable material. In some embodiments of the device, the compartments for containment of vaporizable material 114, 214, 314, with individual resistive heating elements 3, 4, 5 is filled by the user with the same or different vaporizable material. In some embodiments of the device, the compartments for containment of vaporizable material 114, 214, 314, with individual resistive heating elements 3, 4, 5, respectively, are recyclable and/or reusable.

In some embodiments of the device, the compartments for containment of vaporizable material 114, 214, 314, with individual resistive heating elements 3, 4, 5 are replaceable and the housing is reusable.

In some embodiments of the device, a mouthpiece comprises the compartments for containment of vaporizable material 114, 214, 314, with individual resistive heating elements 3, 4, 5, respectively, are replaceable and the mouthpiece is reusable.

The target temperatures for the heating elements 3, 4, 5 may be below the combustion temperature for tobacco. In still other embodiments of the device the target temperatures for the heating elements 3, 4, 5 may be below the pyrolysis temperature for tobacco. More specifically, a target "vapor temperature" is greater than about 100° C., but less than about 300° C., intended to convert the vaporizable material of at least one compartment to a visible vapor.

Still further, in some embodiments the circuitry includes an accelerometer 90 as previously noted. In some embodiments the accelerometer functions comprise; determining if a user is actively using the device, providing a pre-heat condition for the heating elements, providing a battery power level feedback of the device to the user, providing user with a mechanism to change available modes of the device, providing an automatic activation mode when the device is picked up by the user, providing an automatic sleep mode when the device is inactive for a period of time. Direct visual feedback is provided to the user through the use of at least one LED light indicator 20, or Mode indicator 21.

EXAMPLES

A. Components of Final Vapor Separately Stored and Vaporized

Figure 5A:
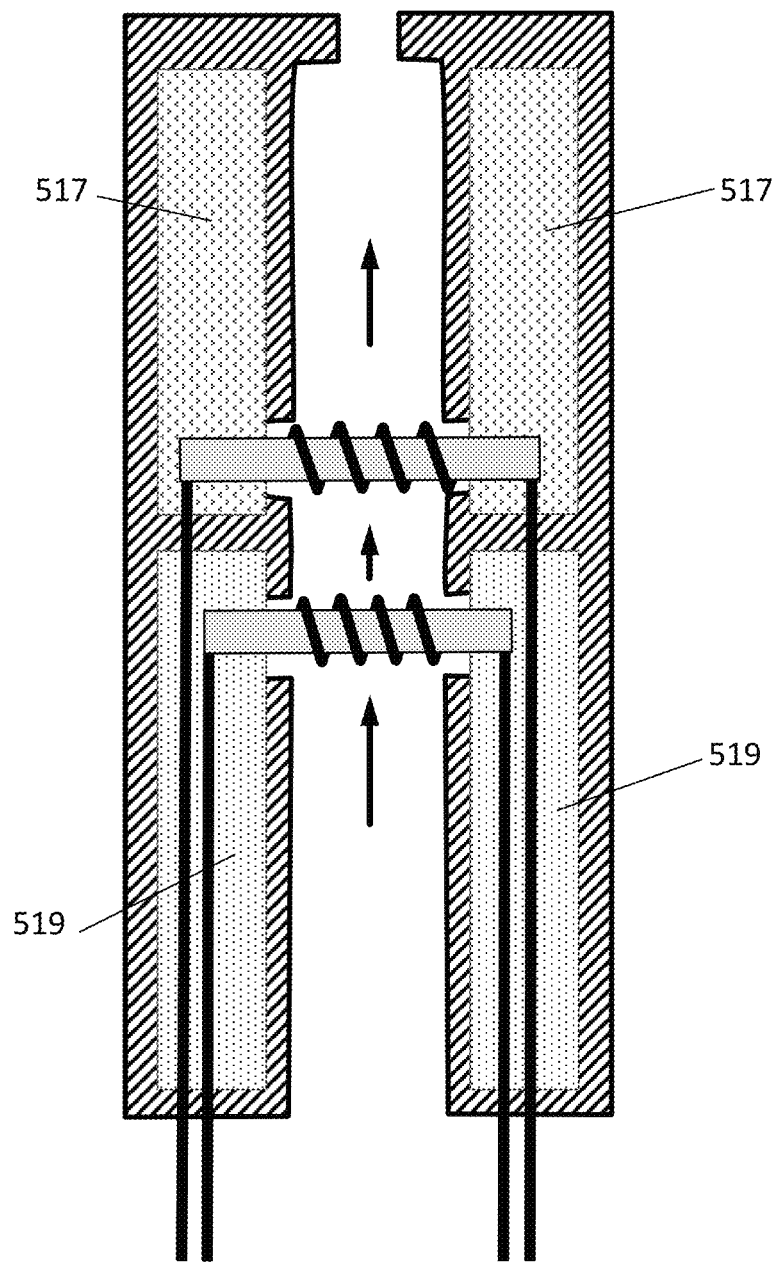
FIG. 5A is an example of a schematic sectional view of another variation of a vaporizer device (e.g., cartridge) in which nicotine is stored separately from an acid or acid precursor and vaporized together, in accordance with some example implementations.

As discussed above, in any of these variations, the vaporizer may separately store and/or vaporize solutions of components of the final vapor. The final vapor may thus be formed by allowing the components to combine in the vapor particles. This may involve particle fusion, elution, etc. For example, in FIGS. 1-3, the separate chambers may include different components of the final vapor. For example, in FIG. 5A, which is similar to FIG. 1, two component regions 517, 519 are each connected to a separate vaporizer. The lower reservoir 519 may include a solution of carrier (biologically acceptable liquid carrier, such as vegetable glycerol and glycol) and freebase nicotine. The upper reservoir 517, may include an acid or acid precursor (a compound that forms an acid when heated, e.g., during vaporization). The acid or acid precursor may also be in the same or a different biologically acceptable liquid carrier (e.g., water). Vapor particles of the carrier and nicotine may be combined with vapor particles of the acid (acid precursor may be converted/degraded to the acid in the vapor particles formed from the material in the upper chamber) to form the final vapor, having particles including nicotine, acid and carrier. Either or both of the component vaporization solutions may include additional components such as flavorants. Alternatively or additionally, FIG. 2 shows an example of a device having a third reservoir that may include a flavorant that when heated forms a vapor that may also combine with the partial components from the other vapor particles to form the final vapor. In the devices shown in FIGS. 1 and 5A the heaters and reservoirs are in series; in some variations, as shown in FIG. 3, the heaters and reservoirs may be arranged in parallel.

One benefit of having separate atomizers (e.g., heaters) as shown in FIGS. 1-3 and 5A-5B is that the devices may be configured to allow a user to adjust the ratio of vapor production between the two, e.g., via a user interface and firmware. This may allow the user to adjust one or more of the amount of nicotine and/or acid, which may adjust (e.g., allow customization) of the nicotine delivered and/or the harshness (or "throat hit") experienced. Increased harshness may correspond to more nicotine deposition in the upper respiratory tract, where nicotine is absorbed into the blood more slowly than in the lung. This could shift from fast acting to sustained absorption, as part of a smoking cessation (e.g., step-down) program, or according to user preference.

Figure 5B:
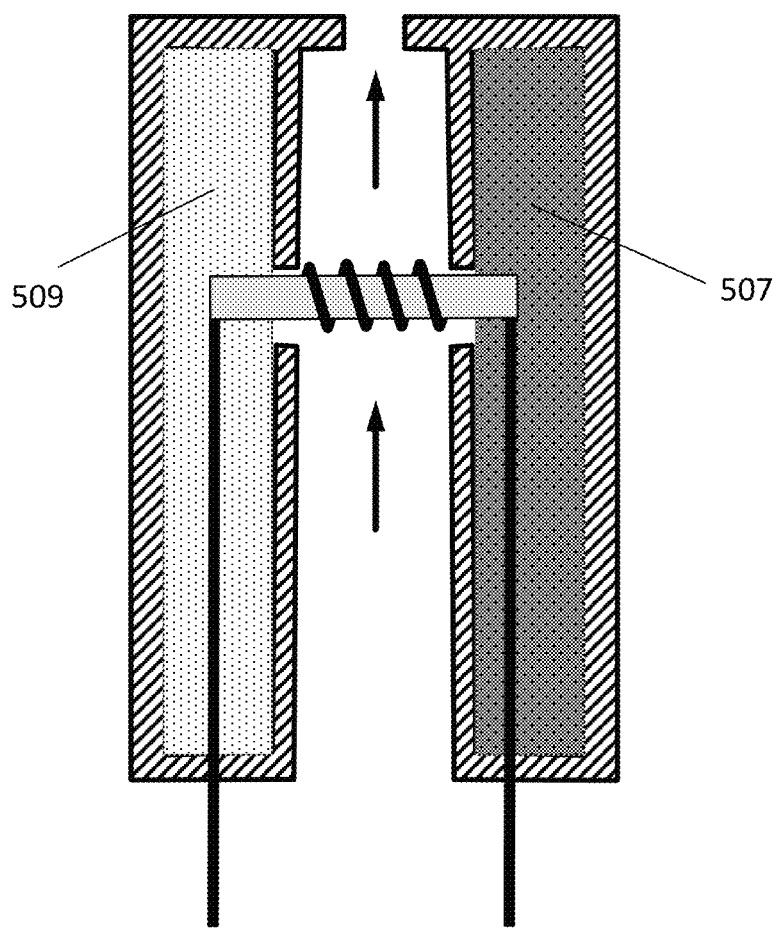
FIG. 5B is an example of a schematic sectional view of another variation of a vaporizer device (e.g., cartridge) in which nicotine (e.g., nicotine and a first carrier) is stored separately from an acid or acid precursor and the two vaporizable materials are vaporized separately but at/near the same time, so that the vapor can combined to form the vapor composition of a nicotine salt, in accordance with some example implementations.

FIG. 5B shows another variation in which two reservoirs 507, 509, one for the freebase nicotine liquid and another for an "acid-only" liquid (e.g., acid or acid precursor) are used. In this example, the two sources of vaporizable materials share the same wick and atomizer, and may therefore combine in/on the wick, during vaporization, and/or after vaporization.

B. Precursor Components

In any of the embodiments described herein, one or more of the component of the vaporizable material to be included in the final composition of the vapor may be in a precursor form that can be converted to a final form during or after vaporization. For example, it may be particularly helpful to maintain an acid as an acid precursor until it can be converted (e.g., during vaporization) into the acid to form the nicotine salt in solution.

An acid precursor may be used (e.g., organic acid precursor) in any of the formulations that will be heated (e.g., for vaporization). For example, an acid precursor may be heated to vaporize the material, and upon heating by the atomizer, the acid precursor may release the acid that serves to protonate nicotine in the aerosol. Any appropriate acid precursor may be used. For example, types of compounds which may produce acids that make nicotine salt formulations when exposed to heat include inorganic salts of the acids (e.g., sodium salts of carboxylic acids), esters of the aids (e.g., ethyl benzoate), and dimers of the acids or their salts (e.g., pyruvic acid dimer).

For example, benzoic acid is one of the thermal decomposition products of sodium benzoate. Pyruvic acid may be produced from sodium pyruvate. Benzoic acid may also be produced from ethyl benzoate by base hydrolysis. Pyruvic acid dimer (or pyruvate salt dimer) is more stable at low temperature and can product pyruvic acid and other acids at high temperatures.

Figure 6A:
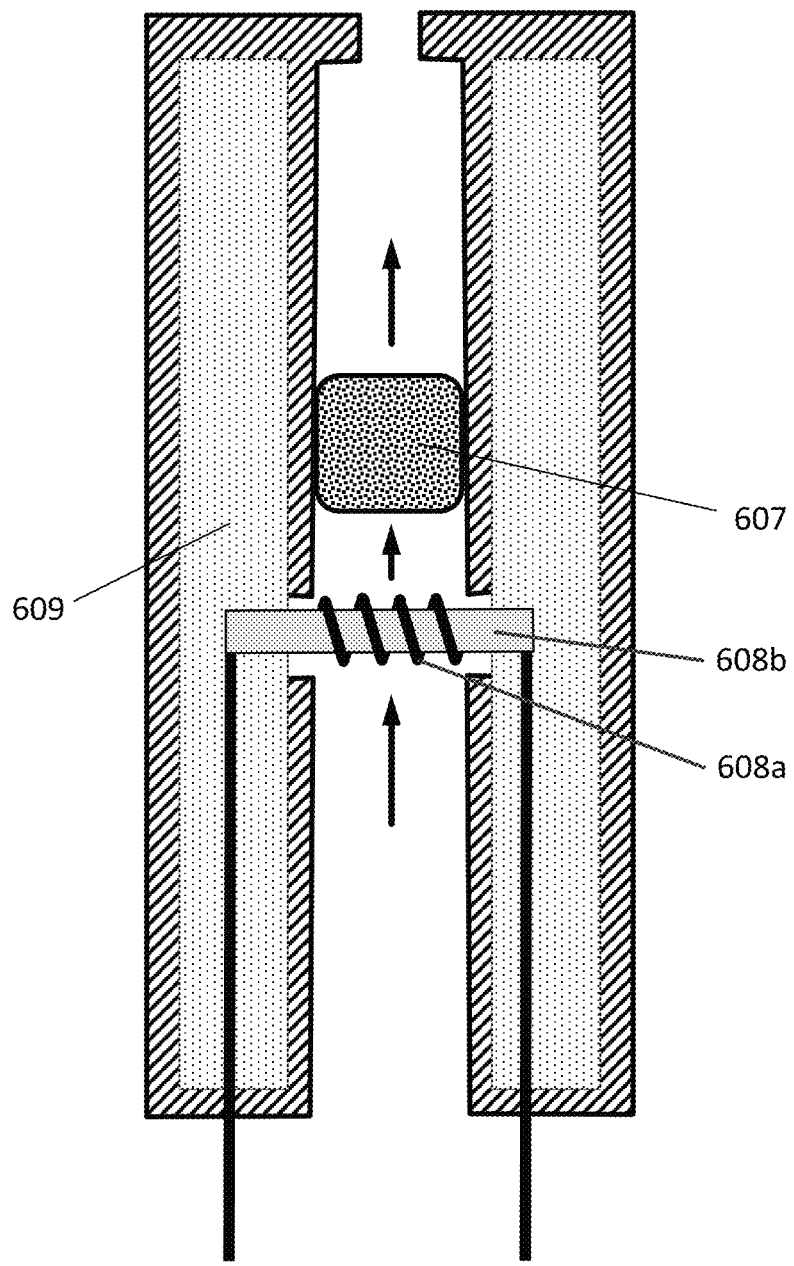
FIG. 6A is a schematic illustration of a vaporizer device including a reservoir of a vaporizable material (e.g., nicotine and a carrier) that is heated to form vapor particles (aerosol particles) that are placed in contact with a porous substrate (e.g., sponge) in that include a liquid solution including another component (e.g., acid) of the final composition of the vapor, in accordance with some example implementations.
Figure 6B:
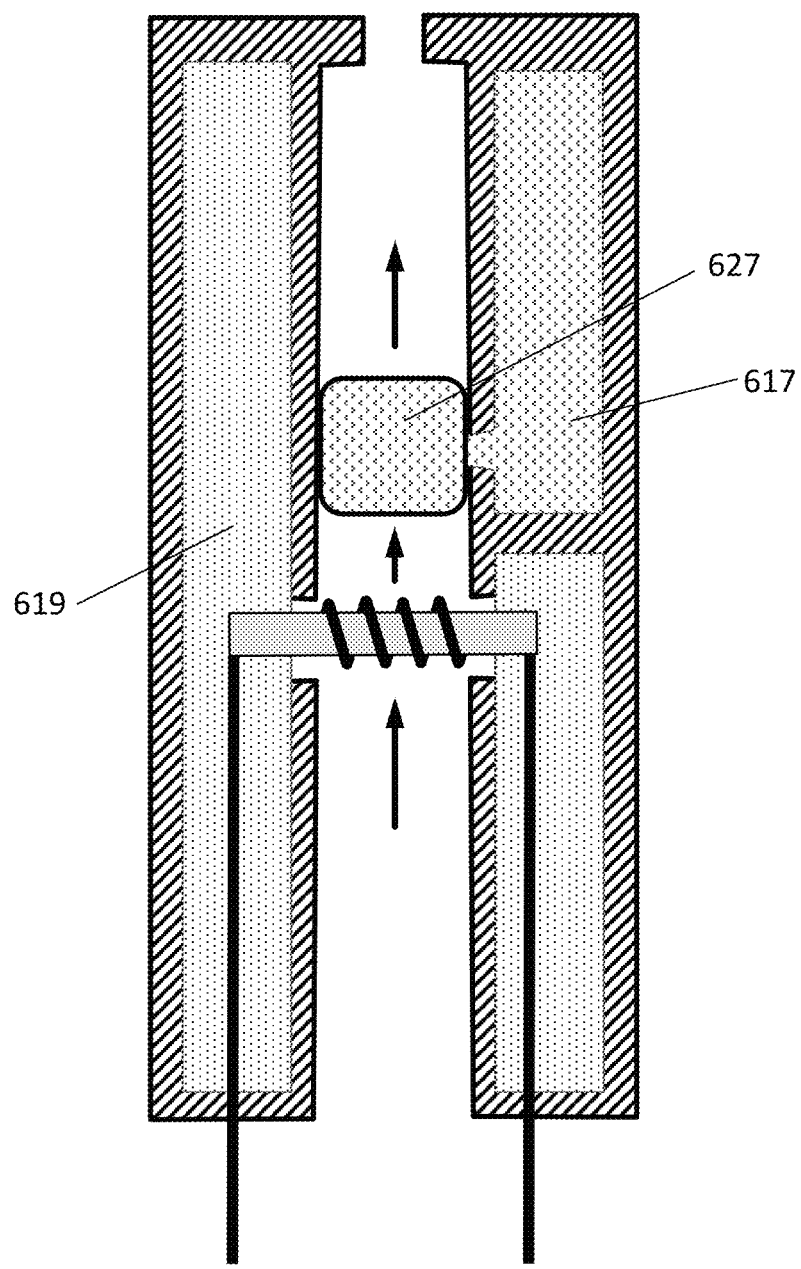
FIG. 6B is similar to FIG. 6B but includes a source of the fluid (e.g., acid or acid precursor) in contact with the porous substrate to keep it wetted during operation, in accordance with some example implementations.
Figure 7:
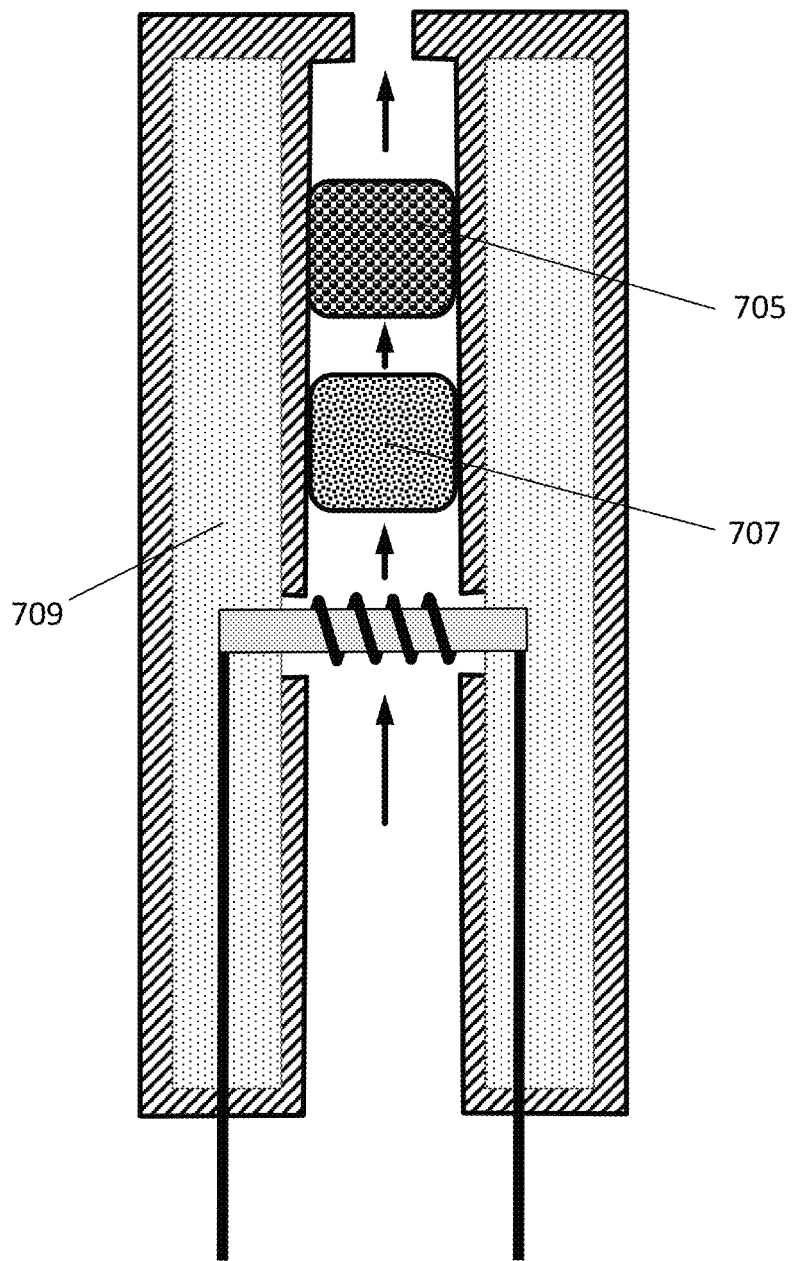
FIG. 7 is a schematic of another variation of a vaporization device with two porous substrates, each including a liquid including a component (e.g., acid or nicotine) to be included in the final vapor composition, in accordance with some example implementations.

C. Elution of Vaporization Material Components from Porous Substrate into Final Vapor FIGS. 6A, 6B and 7 illustrate examples in which a porous substrate 607 (e.g., sponge) is included in the air flow path (draw passage) so that a first vapor formed by the atomizer (e.g., including the heater 608a) from a first material stored in reservoir(s) 609, can combine with/pass through the porous substrate 607 to form the final vapor composition. A combination of the first vapor and a material retained by the sponge 607 can occur through the process of elution. Thus, when delivering protonated nicotine vapor, the acid and nicotine components can be broken out and stored in a porous substrate, such as a sponge 607, in a liquid form. The primary aerosol-forming agent (e.g., a carrier such as glycol) may still be included in the reservoir 609 connected (e.g., by a wick 608b) to the atomizer to form the vapor, in order to volatilize a carrier in quantities sufficient to get a thick aerosol. This aerosol could then be fed through the porous substrate (e.g., sponge) which may be soaked in one or more of the component parts (e.g., nicotine, acid or acid precursor).

The resulting aerosol particles (e.g., aerosols) can be effective at sucking up vapors from adsorbed and/or absorbed liquids through process call elution, so that the final vapor composition includes the absorbed material. In FIG. 6A, for example the liquid reservoir 609 may include carrier (e.g., vegetable glycerol and glycol) and/or at least one of nicotine, acid, and/or acid precursor. A sponge 607 in the draw passage includes a solution of the component(s) not included in the first vaporizable material solution in the reservoir 609, such as acid or nicotine. The final vapor may then include all of the components. In some variations, a single sponge 607 is included and may contain the acid, and the nicotine may be evaporated along with the glycols, or vice-versa. Alternatively, the sponge may include both the nicotine and the acid.

In any of these variations the porous substrate 607 (e.g., sponge) may be connected to a reservoir 609 of solution that keeps the porous substrate "wet" with solution. For example, in FIG. 6B, the sponge 627 contains a solution of either acid or nicotine, in a carrier, and the sponge is connected to a reservoir 617 of this same material.

FIG. 7 shows an example in which two sponges 705, 707 are used, so that separate sponges for the nicotine and/or acid may be present, downstream of the atomizer (heater). As illustrated, a separate reservoir 709 can include a carrier, such as any of the carriers described herein.

Any of the solutions of component vapor materials described herein (nicotine and carrier, acid and carrier) may be warmed, and/or the porous substrate (e.g., sponge) may be warmed. Warming may increase the local vapor and may therefore increase the elution of component material into the vapor particles formed by the heater(s). Warming may be <100° C.

Figure 8:
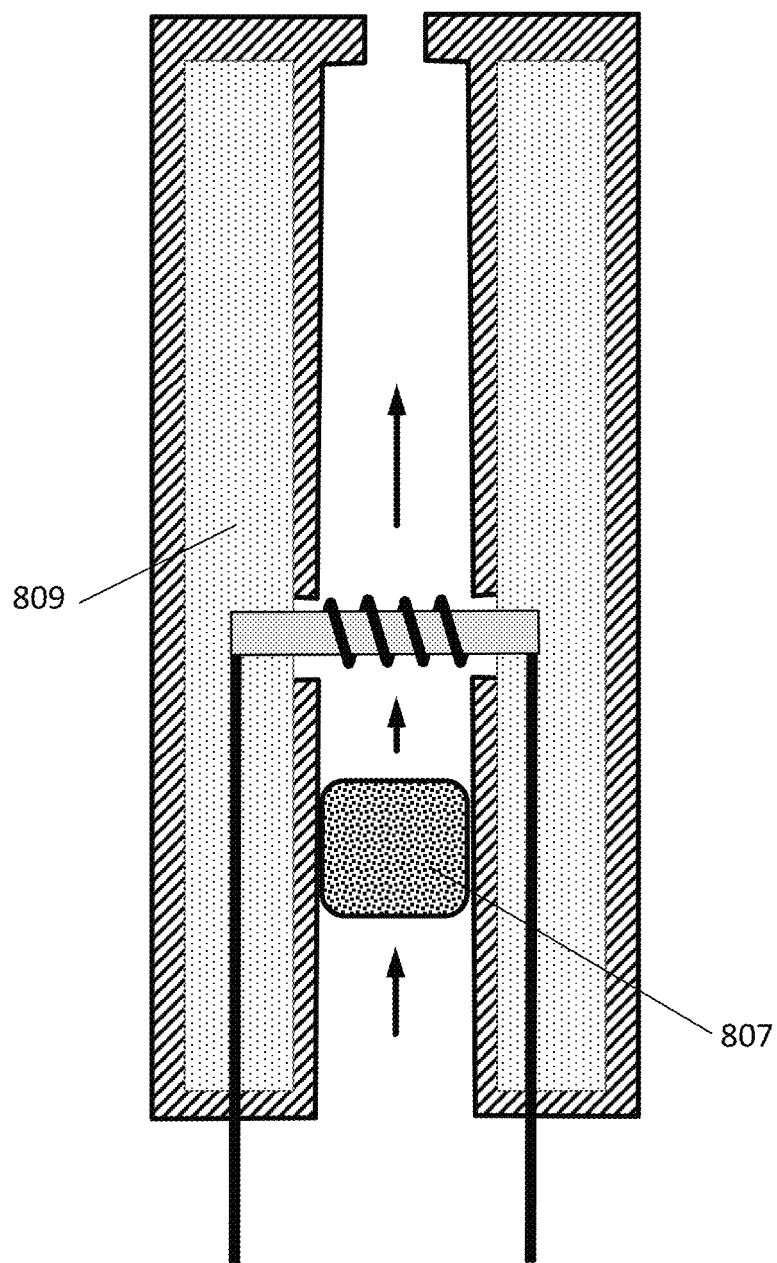
FIG. 8 is another example of a vaporizer device in which a porous substrate (e.g., sponge) is held in the draw channel of the device, but upstream (rather than downstream as shown in FIGS. 6A-7) of the heater forming the vapor, in accordance with some example implementations.

FIG. 8 shows another variation of a device for forming a vapor in which a porous substrate (e.g., sponge 807) is positioned upstream of the atomizer. In this example, air coming in would have to pick up the vapor from the sponge 807 prior to combining with the vapor from the heater (e.g., formed based on a material included in the reservoir(s) 809.

D. Enhancement with Tobacco

Figure 9:
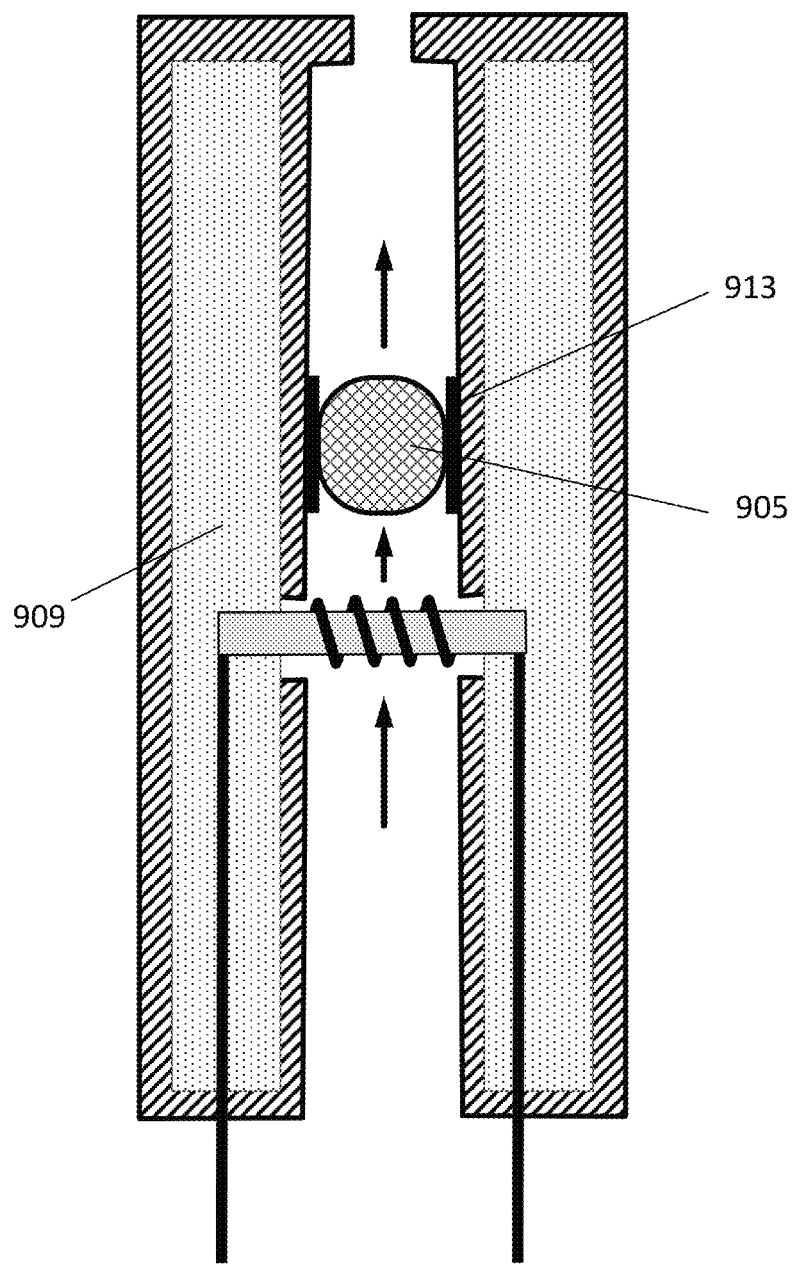
FIG. 9 is an example of a vaporizer including a tobacco material in the draw channel path of the vapor in the device, in accordance with some example implementations.

In any of these variations the apparatus and method may include using tobacco in the airflow path in order to enhance the flavor and/or experience (e.g., to more closely mimic traditional cigarette smoking). For example, FIG. 9 illustrates an example in which a bolus 905 of tobacco material is included in the vapor pathway (draw pathway) so that vapor formed by the device (e.g., based on a material included in the reservoir(s)) will pass through/around the tobacco material. Passing the aerosol through actual tobacco (tobacco material) may extract or impart a rich tobacco flavor. The elution process can pick up flavor compounds from the tobacco, much like in the sponges shown in FIGS. 6-8. As in those example, the tobacco material may be warmed (e.g., conductively, from the sides, and/or via a separate heating element 913), which may improve the flavor uptake. The warming of the tobacco material can be controllable by a user.

E. Vapor Adjustment

In any of these variations the apparatuses and methods described herein, the apparatus of method may be configured to allow the user to adjust the ratio of the vapor's constituents. In general, traditional electronic cigarettes may allow the user to adjust the power output to change the amount of vapor produced in a given inhalation, but this does not affect the ratio of the vapor's constituents. Further, adjusting the power too much can have negative consequences for the user experience and safety. For example, the power can be turned up to the point where some components of the vapor degrade into other substances such as formaldehyde, which may unintentionally change the ratio of vapor components in a negative way. In such devices, in order for a user to alter the vapor's nicotine content, flavor profile, or aerosol visibility, the actual liquid in the e-cigarette's reservoir must be replaced.

There are instances where an e-cigarette user may wish to change the vapor production of his/her device without altering the nicotine delivered per inhalation. For instance, a user driving in a car with others who do not use e-cigarettes and/or are bothered by the vapor, may wish to consume nicotine without bothering other passengers. Current systems have no way to address this issue. In addition, E-cigarette users don't necessarily want the same nicotine strength throughout the day. Someone may prefer a higher nicotine concentration for use during the morning, and a lower nicotine content later in the afternoon/evening. Other systems may achieve this by carrying two separate tanks/atomizers with different nicotine concentrations loaded into each, or by carrying two containers of e-liquid and replacing what was previously in the tank. Refilling a tank almost always causes crossover of the materials. If the wick and coil are not replaced, it will take several inhalations before the previous liquid is evaporated from the wick. Carrying two containers of liquid or a spare tank is ergonomically undesirable. In addition, a spare tank in a pocket will accumulate lint or other contaminants into the tank's air-path and/or electrical connections which is undesirable.

Further, flavor fatigue is a common complaint amongst e-cigarette users. The users may notice that after vaporizing the same flavor for a couple hours, the taste becomes significantly muted, sometimes to the point of not having any flavor. Generally, this requires the user to change the flavor. In current single tank systems, the flavor is changed by changing the tank or changing the liquid in the tank. This presents the same inconveniences preciously covered.

Figure 10:
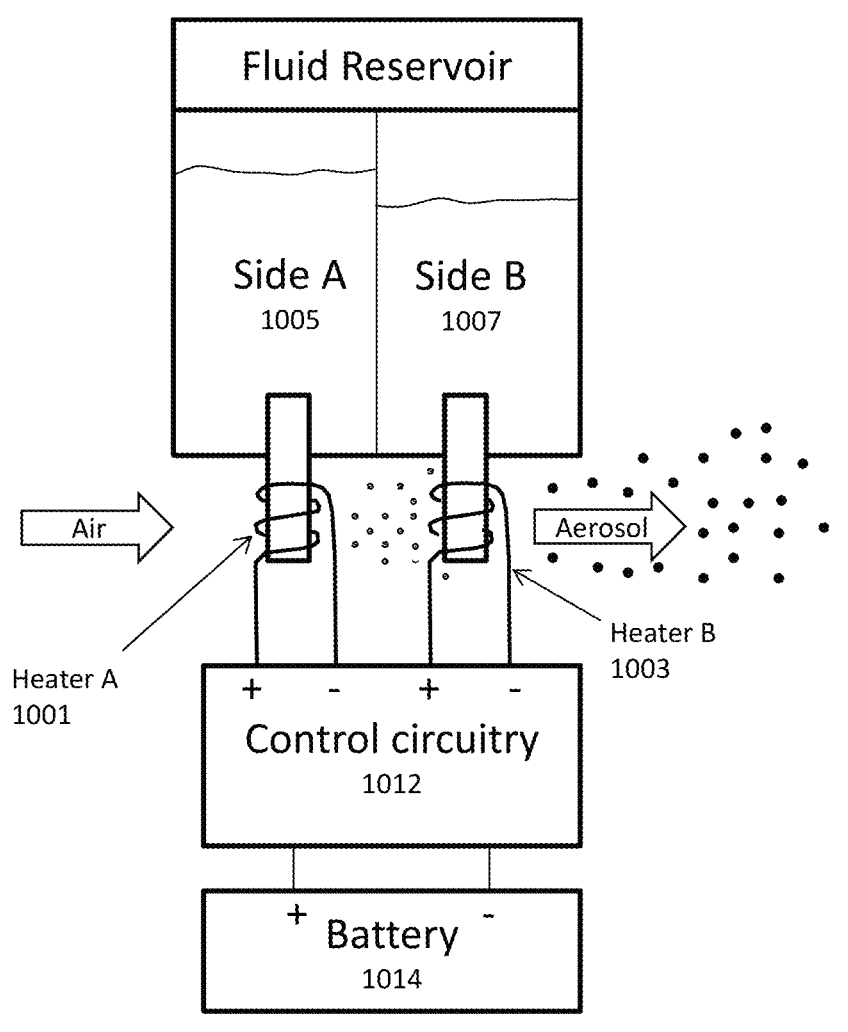

Any of the apparatuses (and methods of using them) described herein may be multi-tank and/or multi-heater electronic cigarettes. FIG. 10 is an illustration of one variation of a dual tank/heater system as described herein. In this example, the apparatus is a multi-tank/heater electronic cigarette (e.g., a dual tank/heater system). The schematic shown in FIG. 10 may refer to a cartridge, e.g., removable from a durable base unit to which different cartridges may be connected.

In FIG. 10, the fluid reservoir is separated into two compartments (Side A 1005, Side B 1007). Each compartment is in fluid communication with its own heater coil (Heater A 1001, Heater B 1003) via a wicking material (e.g., silica, organic cotton, etc.). An air-path may be established in the system, which upon inhalation, draws ambient air over the wicks/heated coils, forming an aerosol containing some ratio of constituents from Side A and B. In FIG. 10 this is shown as the large "air" arrow. The airflow path may be positioned anywhere through the apparatus (e.g., including through the cartridge). Fluid exchange may happen at the wicks, where the loss of fluid from the tank is replaced by air between puffs. The heaters may be controlled individually via a controller including control circuitry (e.g., microcontroller 1012 and battery 1014). Temperature control of the coils can be achieved by using a temperature coefficient of resistance of the coil material to estimate coil temperature. The microcontroller may activate the heater(s) upon user input from a button, breath actuation via pressure sensor, haptic lip sensing, or other means. In addition, since the heaters are powered individually, the controller can control the ratio of power delivered to heater A 1001 versus heater B 1003, or ratio of temperature in a temperature controlled system. This will control the ratio of constituents from side A and B in the final aerosol to be inhaled. This ratio can be adjusted by the user, e.g., with a screen or LED based interface, etc.

Based on how the fluid reservoir is loaded, the percentages (ratios) of different components (e.g., nicotine, acid, flavorant, humectant, etc.) can be adjusted by vaporizing one or the other component separately. For example, if side A is loaded with a high nicotine content (e.g., 10% mass) along with flavor components and humectants, and side B is loaded with just humectants and flavor components, the nicotine strength and/or vapor production can be modulated. Maximum nicotine delivery and vapor production can be achieved by holding heater A and B at maximum appropriate temperature. Maximum nicotine delivery with minimum visible aerosol can be achieved by holding heater A at maximum temperature while not activating heater B. In this example, nicotine delivery itself can be modulated by adjusting the temperature of heater A. Flavor fatigue may be regulated by loading side A with the user's desired nicotine level (e.g., 5% mass), flavor profile A, and humectants, while side B could be loaded with 5% nicotine, flavor profile B, and humectants. Flavor A can be enjoyed by simply holding heater A at max temp and not activating heater B. Flavor B can be enjoyed by doing the inverse. Any blend between the flavors can be had by controlling the temperature ratio between heater A and B. Alternatively or additionally a porous member (e.g., sponge) or the like may be included as well, as described above.

FIG. 11 illustrates an alternative embodiment of a variable aerosol vaporizer similar to the one shown in FIG. 10. This embodiment uses a multi chamber fluid reservoir with a single heater. The reservoir in this system is dual chamber. In this example, the fluid reservoir is separated into two compartments (side A 1118, side B 1119). Each compartment is in fluid communication with the heater 1125 via conduits or capillary tubes. The heater itself can be formed from the conduit material itself if it is metallic, or it can be a traditional wick/coil assembly fed via the conduits. Each conduit may be metered with a valve 1111, 1113, such as a solenoid or piezoelectric valves (Valve A 1111 and B 1113).

An air-path is established in the system, which upon inhalation, draws ambient air over the heater, forming an aerosol containing some ratio of constituents from Side A and B. The reservoir chambers may be pressurized, with constant force springs/pistons for example, to drive fluid flow. Alternatively, the vacuum created by user suction may be solely used to drive fluid flow. In this case, fluid exchange happens at the check valves (A, 1115, and B, 1117) where the loss of fluid from the reservoir chambers is replaced by air during each puff. The heater and valves A and B are controlled via a controller (e.g., control circuitry 1122) and battery 1124. Temperature control of the heater can be had by using the temperature coefficient of resistance of the heater material to estimate heater temperature. The controller (microcontroller and/or other control circuitry) may activate the heater and valve A and/or B upon user input from breath actuation via pressure sensor, haptic lip sensing, or other means. Since valves A and B are controlled individually, the microcontroller can adjust the metering of conduits A and B via pulse width modulation of the valves. This will allow control the ratio of constituents from sides A and B in the final aerosol to be inhaled. As before, the apparatus may optionally be configured to allow the user to adjust ratio can be adjusted by the user interface, e.g., including a screen or LED based interface.

As mentioned, in FIG. 11 and other examples described herein, based on how the fluid reservoir is loaded, each of the problems addressed above can be solved. For example, if side A is loaded with a high nicotine content (e.g., 10% mass) along with flavor components and humectants, and side B is loaded with just humectants and flavor components, the nicotine strength and/or vapor production can be modulated. Maximum nicotine delivery and vapor production can be achieved by pulsing valve A and B at the maximum appropriate duty cycle for the heater's vaporization rate. Maximum nicotine delivery with minimum visible aerosol can be achieved by pulsing valve A at maximum duty cycle while not opening valve B. Nicotine delivery itself can be modulated by adjusting the duty cycle of valve A. Regarding flavor fatigue; side A could be loaded with the user's desired nicotine level (e.g., 5% mass), flavor profile A, and humectants, while side B could be loaded with 5% nicotine, flavor profile B, and humectants. Flavor A can be enjoyed by simply pulsing valve A at max duty cycle and not opening valve B. Flavor B can be enjoyed by doing the inverse. Any blend between the flavors can be had by controlling the duty cycle ratio between valves A and B.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting. For example, as used herein, the terms "aerosol devices," "vaporizer devices," and other variations thereof, are not intended to be limited to just devices which receive and/or utilize cartridges, and may additionally or alternatively refer to the cartridges themselves and/or some portion thereof. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) device, a liquid crystal display (LCD) device, a light emitting diode (LED) device, and/or the like, for displaying/indicating information to the user. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic input, speech input, tactile input, and/or the like. Other possible input devices include touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such phrases are intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." The use of the term "based on," above and in the claims is intended to mean "based at least in part on," such that a feature or element that is not recited is also permissible.

The illustrated methods are exemplary only. Although the methods are illustrated as having a specific operational flow, two or more operations may be combined into a single operation, a single operation may be performed in two or more separate operations, one or more of the illustrated operations may not be present in various implementations, and/or additional operations which are not illustrated may be part of the methods. In addition, the logic flows depicted in the accompanying figures and/or described herein do not necessarily require the particular order shown, or sequential order, to achieve desirable results. Other implementations may be within the scope of the following claims.

What is claimed is:

1. An apparatus comprising:
   a reservoir comprising a liquid barrier defining a compartment containing a liquid vaporizable material;
   a first heater configured to vaporize the liquid vaporizable material to form a first vapor;
   a draw channel configured for passage of the first vapor formed by the first heater, the draw channel defined by a part of the liquid barrier and separated from the compartment by the liquid barrier, the draw channel comprising the first heater; and
   a porous substrate including an elutable material, the porous substrate positioned downstream from the first heater, the porous substrate positioned outside of the compartment and within and across the draw channel such that airflow within the draw channel and the first vapor is passed through the porous substrate in order to exit the draw channel,
   a second heater positioned on an interior surface of the draw channel and in contact with the porous substrate, the second heater configured to heat the elutable material to a temperature that is below a vaporization temperature for the elutable material, and
   wherein an inhalable aerosol is formable by passing the first vapor through the porous substrate and combining the first vapor with the elutable material of the porous substrate, wherein the second heater is positioned downstream of the first heater.

2. The apparatus of claim 1, wherein the liquid vaporizable material comprises about 10-90% vegetable glycerol, and wherein the liquid vaporizable material further comprises propylene glycol.

3. The apparatus of claim 2, wherein the liquid vaporizable material further comprises a flavorant.

4. The apparatus of claim 1, further comprising a controller configured apply energy to the first heater to vaporize the liquid vaporizable material.

5. The apparatus of claim 4, wherein the controller is configured to cause the first heater to heat to between about 100° C. and about 300° C.

6. The apparatus of claim 1, further comprising a cartridge comprising one or more electrical contacts for connection to a controller, wherein the controller is configured to apply energy to the first heater to vaporize the liquid vaporizable material.

7. The apparatus of claim 1, wherein the inhalable aerosol is formable based on elution of at least a portion of the elutable material.

8. The apparatus of claim 1, wherein the elutable material comprises at least one of a tobacco material or a botanical.

9. The apparatus of claim 1, wherein the liquid vaporizable material comprises (i) nicotine and (ii) an acid or acid precursor that forms an acid upon heating.

10. The apparatus of claim 1, wherein the liquid vaporizable material comprises between 0.5% and 20% nicotine.

11. The apparatus of claim 1, wherein the inhalable aerosol includes particles comprising from about 0.5% (w/w) to about 20% (w/w) protonated nicotine, an acid, and a carrier.

12. The apparatus of claim 1, wherein the inhalable aerosol comprises nicotine.

13. The apparatus of claim 1,
   wherein the elutable material comprises one or more of an acid and nicotine.

14. The apparatus of claim 1, further comprising:
   an aerosol outlet configured to allow for passage of the inhalable aerosol for inhalation by a user.

15. A method comprising:
   vaporizing, using a first heater, at least a portion of a liquid vaporizable material to form a first vapor, wherein the liquid vaporizable material is stored in a reservoir coupled to the first heater, the reservoir comprising a liquid barrier defining a compartment containing the liquid vaporizable material, and wherein the first heater is positioned within a draw channel defined by a part of the liquid barrier and separated from the compartment by the liquid barrier;

heating a porous substrate including an elutable material to a temperature that is below a vaporization temperature for the elutable material with a second heater, the second heater positioned on an interior surface of the draw channel and in contact with the porous substrate; and forming an inhalable aerosol by passing the first vapor through the porous substrate including the elutable material and combining the first vapor with the elutable material of the porous substrate, the porous substrate positioned outside of the compartment and downstream from the first heater, the porous substrate positioned within and across the draw channel such that airflow within the draw channel and the first vapor is passed through the porous substrate in order to exit the draw channel, wherein the second heater is positioned downstream of the first heater.

16. The method of claim 15, wherein the elutable material comprises a tobacco material, and the porous substrate is positioned between the first heater and an aerosol outlet of the draw channel.

17. The apparatus of claim 1, wherein the porous substrate is positionable between the first heater and an air outlet of the draw channel.

18. The apparatus of claim 1, further comprising a detachable cartridge and a reusable body coupled to the cartridge, wherein the cartridge comprises the reservoir, the first heater, the draw channel, the elutable material, and the second heater, and the reusable body includes a battery and circuitry connected to the battery.

19. The apparatus of claim 1, wherein the draw channel is a single airpath extending between an inlet positioned upstream from the first heater and an outlet of the apparatus, the outlet being downstream from the porous substrate positioned within and across the draw channel.

* * * * *